United States Patent
Dakappagari et al.

(10) Patent No.: US 11,726,092 B2
(45) Date of Patent: *Aug. 15, 2023

(54) METHOD OF SCORING A SAMPLE COMPRISING TUMOR TISSUE

(71) Applicant: Novartis AG, Basel (CH)

(72) Inventors: Naveen Dakappagari, Carlsbad, CA (US); Thai Tran, Carlsbad, CA (US); Brian Little, Carlsbad, CA (US); Ju Young Kim, Carlsbad, CA (US); Jennifer Bordeaux, Carlsbad, CA (US)

(73) Assignee: Novartis AG, Basel (CH)

( * ) Notice: Subject to any disclaimer, the term of this patent is extended or adjusted under 35 U.S.C. 154(b) by 454 days.

This patent is subject to a terminal disclaimer.

(21) Appl. No.: 16/890,835

(22) Filed: Jun. 2, 2020

(65) Prior Publication Data

US 2020/0292550 A1 Sep. 17, 2020

Related U.S. Application Data

(63) Continuation of application No. 15/768,849, filed as application No. PCT/US2016/058281 on Oct. 21, 2016, now Pat. No. 10,705,088.

(60) Provisional application No. 62/259,319, filed on Nov. 24, 2015, provisional application No. 62/245,858, filed on Oct. 23, 2015.

(51) Int. Cl.
*G01N 33/574* (2006.01)
*G06T 7/00* (2017.01)

(52) U.S. Cl.
CPC . *G01N 33/57492* (2013.01); *G01N 33/57484* (2013.01); *G06T 7/0012* (2013.01); *G01N 2333/70521* (2013.01); *G01N 2800/52* (2013.01); *G01N 2800/60* (2013.01); *G06T 2207/10064* (2013.01); *G06T 2207/30096* (2013.01)

(58) Field of Classification Search
CPC ... G01N 33/57492; G01N 2333/70521; G01N 2800/52; G01N 2800/60
See application file for complete search history.

(56) References Cited

U.S. PATENT DOCUMENTS

| 6,259,807 | B1 | 7/2001 | Ravkin | |
|---|---|---|---|---|
| 2014/0323907 | A1* | 10/2014 | Frazier | A61M 5/00 604/93.01 |
| 2018/0299030 | A1 | 10/2018 | Vandlik et al. | |

FOREIGN PATENT DOCUMENTS

| JP | 2018-521284 A | 8/2018 |
|---|---|---|
| WO | WO 94/13834 | 6/1994 |
| WO | WO 2015/088930 A1 | 6/2015 |

OTHER PUBLICATIONS

Lathia, et al., "Direct In Vivo Evidence for Tumor Propagation by Glioblastoma Cancer Stem Cells," *PLoS One*, vol. 6, No. 9(e24807), pp. 1-9 (Sep. 2011).

(Continued)

*Primary Examiner* — Mark Halvorson
*Assistant Examiner* — Dennis J Sullivan
(74) *Attorney, Agent, or Firm* — Foley & Lardner LLP

(57) ABSTRACT

The invention relates, in part, to methods of scoring a sample containing tumor tissue from a cancer patient. The score is representative of a spatial proximity between at least one pair of cells, a first member of the at least one pair of cells expressing a first biomarker and a second member of the at least one pair of cells expressing a second biomarker that is different from the first biomarker. The score obtained from these methods can be indicative of a likelihood that a patient may respond positively to immunotherapy.

20 Claims, 21 Drawing Sheets

(56) References Cited

OTHER PUBLICATIONS

Dieck, et al., Direct Visualization of Newly Synthesized Target Proteins in Situ., *Nat. Methods.*, vol. 12, No. 5, pp. 411-414 (May 2015).

Ljosa, et al., "Introduction to the Quantitative Analysis of Two-Dimensional Fluorescence Microscopy Images for Cell-Based Screening," *PLoS Computational Biology*, vol. 5, No. 12(e1000603), pp. 1-10 (Dec. 2009).

Cancer Immunotherapy and the PD1/PDL1 Checkpoint Pathway—Abcam [accessed Mar. 25, 2022] published on Oct. 5, 2015 as per The Wayback Machine, 3 pages.

Chen, et al., "Anti-PD-1/PD-L1 Therapy of Human Cancer: Past, Present, and Future," *The Journal of Clinical Investigation*, vol. 125, No. 9, pp. 3384-3391 (Sep. 2015).

He, et al., "Development of PD-1/PD-L1 Pathway in Tumor Immune Microenvironment and Treatment for Non-Small Cell Lung Cancer," *Scientific Reports*, vol. 5, No. 1, pp. 1-9 (Aug. 2015).

Examination Report issued in Australian Patent Application No. 2016341307, dated Mar. 21, 2022.

Yuan et al., "Quantitative Image Analysis of Cellular Heterogeneity in Breast Tumors Complements Genomic Profiling," *Science Translational Medicine*, vol. 4, No. 157, pp. 1-10 (Oct. 2012).

Kerr et al., "Programmed Death-Ligand 1 Immunohistochemistry in Lung Cancer: In What State is this Art?," *Journal of Thoracic Oncology*, vol. 10, No. 7, pp. 985-989 (Jul. 2015).

International Search Report and Written Opinion issued in related International Patent Application No. PCT/US2016/058281, dated Mar. 13, 2017.

Tumeh, et al., "PD-1 Blockade Induces Responses by Inhibiting Adaptive Immune Resistance," *Nature*, vol. 515, No. 7528, pp. 568-571 (2014).

Supplemental European Search Report issued in co-pending European Patent Application No. 16 85 8377 dated Apr. 26, 2019.

International Preliminary Report on Patentability issued in co-pending International Patent Application No. PCT/US2016/058281, dated Mar. 13, 2017.

Grounds for Rejection issued in co-pending Japanese Patent Application No. 2020-134749, dated Jun. 29, 2021.

\* cited by examiner

METHOD OF SCORING A SAMPLE COMPRISING TUMOR TISSUE

CROSS-REFERENCE TO RELATED APPLICATIONS

This application is a continuation of U.S. patent application Ser. No. 15/768,849, filed Apr. 17, 2018, which is the U.S. National Stage of International Patent Application No. PCT/US2016/058281, filed Oct. 21, 2016, which claims priority from U.S. Provisional Patent Application No. 62/245,858, filed on Oct. 23, 2015, and U.S. Provisional Patent Application No. 62/259,319, filed on Nov. 24, 2015, all of which are hereby incorporated by reference in their entirety.

BACKGROUND

The present invention relates generally to the field of cancer treatment.

SUMMARY

Disclosed herein, in one aspect, are methods of scoring a sample comprising tumor tissue taken from a cancer patient comprising: (i) using the sample comprising tumor tissue taken from the cancer patient, determining a score representative of a spatial proximity between at least one pair of cells, a first member of the at least one pair of cells expressing a first biomarker and a second member of the at least one pair of cells expressing a second biomarker that is different from the first biomarker; and (ii) recording the score, which score when compared to a threshold value is indicative of a likelihood that the cancer patient will respond positively to immunotherapy. In some embodiments, the first member of the at least one pair of cells comprises a tumor cell and the second member of the at least one pair of cells comprises a non-tumor cell. In some embodiments, the non-tumor cell comprises an immune cell. In some embodiments, the first and second members of the at least one pair of cells comprise immune cells. In some embodiments, the first member of the at least one pair of cells comprises a tumor cell, a myeloid cell, or a stromal cell and the second member of the at least one pair of cells comprises an immune cell. In some embodiments, the tumor cell, myeloid cell, or stromal cell expresses PD-L1 and the immune cell expresses PD-1. In some embodiments, the spatial proximity is assessed on a pixel scale. In some embodiments, the spatial proximity between the at least one pair of cells ranges from about 1 pixel to about 100 pixels. In some embodiments, the spatial proximity between the at least one pair of cells ranges from about 0.5 µm to about 50 µm. In some embodiments, the determining step comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin sufficient to encompass proximally located cells expressing the second biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, each of the fluorescence tags is directed to a specific biomarker. In some embodiments, the plurality of fluorescence tags comprises a first fluorescence tag for the first biomarker and a second fluorescence tag for the second biomarker. In some embodiments, the margin ranges from about 1 to about 100 pixels. In some embodiments, the proximally located cells expressing the second biomarker are within about 0.5 to about 50 µm of a plasma membrane of the cells that express the first biomarker. In some embodiments, the first total area is measured in pixels. In some embodiments, the normalization factor is a second total area for all non-tumor cells from each of the selected fields of view. In some embodiments, the normalization factor is a second total area for all cells from each of the selected fields of view which have a capacity to express the second biomarker. In some embodiments, the normalization factor is a second total area for all cells from each of the selected fields of view. In some embodiments, the second total area is measured in pixels. In some embodiments, the predetermined factor is $10^4$. In some embodiments, the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof. In some embodiments, the first member of the at least one pair of cells expresses PD-L1 and the second member of the at least one pair of cells expresses PD-1. In some embodiments, the first member of the at least one pair of cells expresses PD-L1 and the second member of the at least one pair of cells expresses CD80. In some embodiments, the first member of the at least one pair of cells expresses CTLA-4 and the second member of the at least one pair of cells expresses CD80. In some embodiments, the first member of the at least one pair of cells expresses PD-L2 and the second member of the at least one pair of cells expresses PD-1. In some embodiments, the first member of the at least one pair of cells expresses CTLA-4 and the second member of the at least one pair of cells expresses CD86. In some embodiments, the first member of the at least one pair of cells expresses LAG-3 and the second member of the at least one pair of cells expresses HLA-DR. In some embodiments, the first member of the at least one pair of cells expresses TIM-3 and the second member of the at least one pair of cells expresses Galectin 9. In some embodiments, the first member of the at least one pair of cells expresses 41BB and the second member of the at least one pair of cells expresses 4.1BBL. In some embodiments, the first member of the at least one pair of cells expresses OX40 and the second member of the at least one pair of cells expresses OX40L. In some embodiments, the first member of the at least one pair of cells expresses CD40 and the second member of the at least one pair of cells expresses CD40L. In some embodiments, the first member of the at least one pair of cells expresses ICOS and the second member of the at least one pair of cells expresses ICOSL. In some embodiments, the first member of the at least one pair of cells expresses GITR and the second member of the at least one pair of cells expresses GITRL. In some embodiments, the first member of the at least one pair of cells expresses HLA-DR and the second member of the at least one pair of cells expresses TCR. In some embodiments, the threshold value ranges from about 500 to about 5000. In some embodiments, the threshold value is about 900 plus or minus 100. In some embodiments, the immunotherapy comprises immune checkpoint therapy. In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are methods of determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from a sample comprising tumor tissue taken from a cancer patient, which is stained with a plurality of fluorescence tags, which selection is biased toward selecting fields of view that contain a greater number of cells that express a first specific biomarker relative to other fields of view; (ii) for each of the selected fields of view, dilating fluorescence signals attributable to the first specific biomarker by a margin sufficient to encompass proximally located cells expressing a second specific biomarker; and (iii) dividing a first total area for all cells from each of the selected fields of view, which express the second specific biomarker and are encompassed within the dilated fluorescence signals attributable to the cells expressing the first specific biomarker, with a normalization factor, and multiplying the resulting quotient by a predetermined factor to arrive at a spatial proximity score. In some embodiments, each of the fluorescence tags is directed to a specific biomarker. In some embodiments, the plurality of fluorescence tags comprises a first fluorescence tag for the first biomarker and a second fluorescence tag for the second biomarker. In some embodiments, one or more fluorescence tags comprise a fluorophore conjugated to an antibody having a binding affinity for a specific biomarker or another antibody. In some embodiments, each fluorescence tag comprises a fluorophore independently selected from one or more of the group consisting of DAPI, Cy® 2, Cy® 3, Cy® 3.5, Cy® 5, FITC, TRITC, a 488 dye, a 555 dye, a 594 dye, and Texas Red. In some embodiments, the margin ranges from about 1 to about 100 pixels. In some embodiments, the proximally located cells expressing the second specific biomarker are within about 0.5 to about 50 µm of a plasma membrane of the cells that express the first specific biomarker. In some embodiments, the first total area is measured in pixels. In some embodiments, the normalization factor is a second total area for all non-tumor cells from each of the selected fields of view. In some embodiments, the normalization factor is a second total area for all cells from each of the selected fields of view which have a capacity to express the second specific biomarker. In some embodiments, the normalization factor is a second total area for all cells from each of the selected fields of view. In some embodiments, the second total area is measured in pixels. In some embodiments, the predetermined factor is $10^4$. In some embodiments, the spatial proximity score (SPS) is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker. In some embodiments, the method provides a superior predictive power compared to quantitation of expression of the first specific biomarker or quantitation of expression of the second specific biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In some embodiments, the first specific biomarker comprises a tumor and non-tumor marker and the second specific biomarker comprises a non-tumor marker.

BRIEF DESCRIPTION OF THE DRAWINGS

FIG. 2b shows a non-limiting example of a dilated binary mask of all cells within FIG. 2a.

FIG. 3b shows a non-limiting example of a binary mask of all tumor area within FIG. 3a.

FIG. 3c shows a non-limiting example of a mask of all tumor cells within FIG. 3a.

FIG. 3d shows a non-limiting example of a mask of all non-tumor cells within FIG. 3a.

FIG. 4b shows a non-limiting example of a binary mask of all PD-L1-positive cells within FIG. 4a.

FIG. 5b shows a non-limiting example of a binary mask of all PD-1-positive non-tumor cells within FIG. 5a.

FIG. 7b shows a non-limiting example of the maximum interaction scores from the 26 patients of FIG. 7a.

FIG. 19b shows a comparison of interaction scores with progression free survival of the patients of FIG. 19a.

FIG. 19c shows the interaction scores from the patients of FIG. 7 and the patients of FIG. 19a.

DETAILED DESCRIPTION

Figure 1:
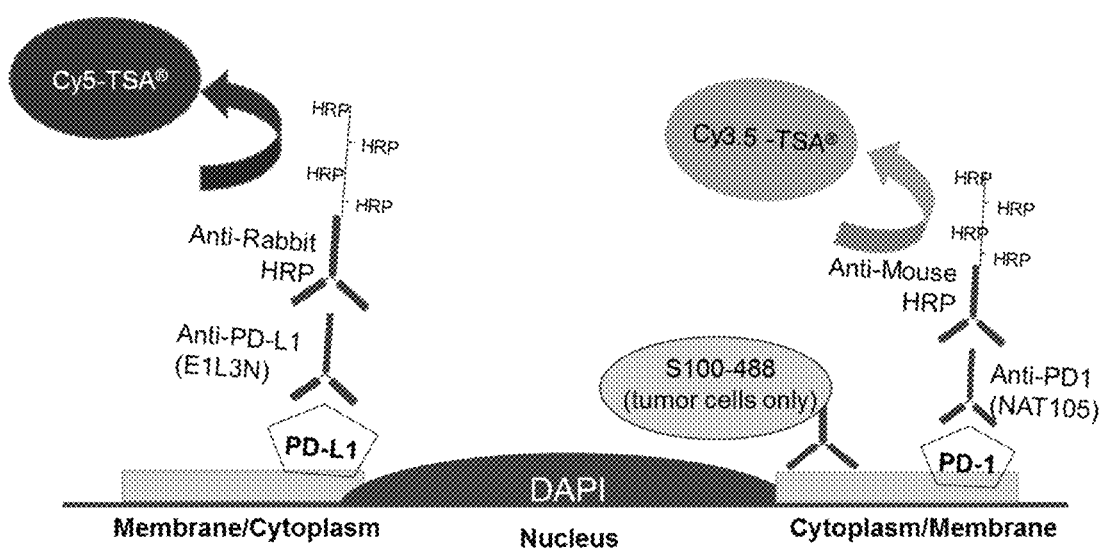
FIG. 1 shows a non-limiting example of an overview of antibodies and detection reagents used in the preparation of tissue samples for imaging and analysis.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

In one aspect, provided herein are methods of scoring a sample comprising tumor tissue taken from a cancer patient.

In some embodiments, the sample may be stained using a plurality of fluorescence tags with affinity for specific biomarkers. A digital image of the stained sample may be obtained, and the image further analyzed based on the location of the fluorescence tags. Rather than whole-image analysis, fields of view may be prioritized based on the number of cells that express a first biomarker of interest. A predetermined number of fields of view may then be further analyzed for fluorescence signals. In some embodiments, the use of four different types of fluorescence tags generates an image of fluorescence signals corresponding to a first biomarker of interest and an image of fluorescence signals corresponding a second biomarker of interest as well as to an image of fluorescence signals corresponding a biomarker expressed by all cells and an image of fluorescence signals corresponding a biomarker expressed by tumor cells. In further embodiments, the images of fluorescence signals are manipulated to generate one or more masks of fluorescence signals corresponding to cells within the image. In some embodiments, the one or more masks of fluorescence signals comprise one or more selected from the group consisting of a mask of all cells within the image, a mask of all tumor cells within the image, a mask of all non-tumor cells within the image, a mask of all cells expressing a first biomarker of interest within the image, a mask of all cells expressing a second biomarker of interest within the image, and an interaction mask representing all cells expressing a first biomarker of interest within the image as well as proximally located cells expressing a second biomarker of interest. In still further embodiments, the interaction mask is used to generate an interaction compartment of the cells from all selected fields of view expressing the second biomarker of interest that were proximally located to the cells expressing the first biomarker of interest. The total area of the interaction compartment may be used to generate a score representative of a spatial proximity between at least one pair of cells, a first member of the at least one pair of cells expressing the first biomarker and a second member of the at least one pair of cells expressing the second biomarker that is different from the first biomarker. In some embodiments, the score indicates the likelihood that the cancer patient will respond positively to immunotherapy. In some embodiments, the method provides a superior predictive power compared to a quantitation of expression of the first biomarker of interest or a quantitation of expression of the second biomarker of interest.

Accordingly, in some embodiments, provided herein are methods of scoring a sample comprising tumor tissue taken from a cancer patient comprises: (i) using the sample comprising tumor tissue taken from the cancer patient, determining a score representative of a spatial proximity between at least one pair of cells, a first member of the at least one pair of cells expressing a first biomarker and a second member of the at least one pair of cells expressing a second biomarker that is different from the first biomarker; and (ii) recording the score, which score when compared to a threshold value is indicative of a likelihood that the cancer patient will respond positively to immunotherapy. In some embodiments, the method provides a superior predictive power compared to a quantitation of expression of the first biomarker or a quantitation of expression of the second biomarker.

In some embodiments, the first member of the at least one pair of cells comprises a tumor cell and the second member of the at least one pair of cells comprises a non-tumor cell. In some embodiments, the non-tumor cell is an immune cell. In some embodiments, the non-tumor cell is a stromal cell.

In some embodiments, the first and second members of the at least one pair of cells comprise immune cells.

In some embodiments, the first member of the at least one pair of cells comprises a tumor cell, a myeloid cell, or a stromal cell and the second member of the at least one pair of cells comprises an immune cell. In some embodiments, the tumor cell, myeloid cell, or stromal cell expresses PD-L1 and the immune cell expresses PD-1.

In some embodiments, the first member of the at least one pair of cells comprises a tumor cell and the second member of the at least one pair of cells comprises an immune cell. In some embodiments, the first member of the at least one pair of cells comprises a myeloid cell and the second member of the at least one pair of cells comprises an immune cell. In some embodiments, the first member of the at least one pair of cells comprises a stromal cell and the second member of the at least one pair of cells comprises an immune cell. In some embodiments, the first member of the at least one pair of cells expresses PD-L1 and the immune cell expresses PD-1.

In some embodiments, the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, GITRL, and combinations thereof. In some embodiments, the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof. In some embodiments, the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof.

In some embodiments, the first member of the at least one pair of cells expresses PD-L1 and the second member of the at least one pair of cells expresses PD-1. In some embodiments, the first member of the at least one pair of cells expresses PD-L1 and the second member of the at least one pair of cells expresses CD80. In some embodiments, the first member of the at least one pair of cells expresses CTLA-4 and the second member of the at least one pair of cells expresses CD80. In some embodiments, the first member of the at least one pair of cells expresses PD-L2 and the second member of the at least one pair of cells expresses PD-1. In some embodiments, the first member of the at least one pair of cells expresses CTLA-4 and the second member of the at least one pair of cells expresses CD86. In some embodiments, the first member of the at least one pair of cells expresses LAG-3 and the second member of the at least one pair of cells expresses HLA-DR. In some embodiments, the first member of the at least one pair of cells expresses TIM-3 and the second member of the at least one pair of cells expresses Galectin 9. In some embodiments, the first member of the at least one pair of cells expresses 41BB and the second member of the at least one pair of cells expresses 4.1BBL. In some embodiments, the first member of the at least one pair of cells expresses OX40 and the second member of the at least one pair of cells expresses OX40L. In some embodiments, the first member of the at least one pair of cells expresses CD40 and the second member of the at least one pair of cells expresses CD40L. In some embodiments, the first member of the at least one pair of cells expresses ICOS and the second member of the at least one pair of cells expresses ICOSL. In some embodiments, the first member of the at least one pair of cells expresses GITR and the second member of the at least one pair of cells expresses GITRL. In some embodiments, the first member of the at least one pair of cells expresses HLA-DR and the second member of the at least one pair of cells expresses TCR.

In some embodiments, the first biomarker expressed by the first member of the at least one pair of cells and the second biomarker expressed by the second member of the at least one pair of cells interact with one another. In some embodiments, the first biomarker expressed by the first member of the at least one pair of cells and the second biomarker expressed by the second member of the at least one pair of cells do not interact with one another.

In some embodiments, the spatial proximity between the at least one pair of cells ranges from about 0.5 µm to about 50 µm. In some embodiments, the spatial proximity ranges from 2.5 µm to about 50 µm. In some embodiments, the spatial proximity ranges from 2.5 µm to about 45 µm. In some embodiments, the spatial proximity ranges from 2.5 µm to about 40 µm. In some embodiments, the spatial proximity ranges from 2.5 µm to about 35 µm. In some embodiments, the spatial proximity ranges from 2.5 µm to about 30 µm. In some embodiments, the spatial proximity ranges from 2.5 µm to about 25 µm. In some embodiments, the spatial proximity ranges from 2.5 µm to about 20 µm. In some embodiments, the spatial proximity ranges from 2.5 µm to about 15 µm. In some embodiments, the spatial proximity ranges from 5 µm to about 50 µm. In some embodiments, the spatial proximity ranges from 5 µm to about 45 µm. In some embodiments, the spatial proximity ranges from 5 µm to about 40 µm. In some embodiments, the spatial proximity ranges from 5 µm to about 35 µm. In some embodiments, the spatial proximity ranges from 5 µm to about 30 µm. In some embodiments, the spatial proximity ranges from 5 µm to about 25 µm. In some embodiments, the spatial proximity ranges from 5 µm to about 20 µm. In some embodiments, the spatial proximity ranges from 5 µm to about 15 μm. In some embodiments, the spatial proximity is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm.

In some embodiments, the spatial proximity between the at least one pair of cells ranges from about 1 pixel to about 100 pixels. In some embodiments, the spatial proximity ranges from about 5 to about 100 pixels. In some embodiments, the spatial proximity ranges from about 5 to about 90 pixels. In some embodiments, the spatial proximity ranges from about 5 to about 80 pixels. In some embodiments, the spatial proximity ranges from about 5 to about 70 pixels. In some embodiments, the spatial proximity ranges from about 5 to about 60 pixels. In some embodiments, the spatial proximity ranges from about 5 to about 50 pixels. In some embodiments, the spatial proximity ranges from about 5 to about 40 pixels. In some embodiments, the spatial proximity ranges from about 5 to about 30 pixels. In some embodiments, the spatial proximity ranges from about 10 to about 100 pixels. In some embodiments, the spatial proximity ranges from about 10 to about 90 pixels. In some embodiments, the spatial proximity ranges from about 10 to about 80 pixels. In some embodiments, the spatial proximity ranges from about 10 to about 70 pixels. In some embodiments, the spatial proximity ranges from about 10 to about 60 pixels. In some embodiments, the spatial proximity ranges from about 10 to about 50 pixels. In some embodiments, the spatial proximity ranges from about 10 to about 40 pixels. In some embodiments, the spatial proximity ranges from about 10 to about 30 pixels. In some embodiments, the spatial proximity is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 pixels. In some embodiments, a pixel is 0.5 μm wide.

In some embodiments, the determining step comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin sufficient to encompass proximally located cells expressing the second biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, the determining step comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker to encompass proximally located cells expressing the second biomarker within about 0.5 μm to about 50 μm of a plasma membrane of the cells that express the first biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, the determining step comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin ranging from about 1 to about 100 pixels to encompass proximally located cells expressing the second biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, the determining step comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin ranging from about 1 to about 100 pixels to encompass cells expressing the second biomarker within about 0.5 μm to about 50 μm of a plasma membrane of the cells that express the first biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, four fluorescence tags, each specific to a different biomarker, are used in the determining step. In further embodiments, a first fluorescence tag is associated with the first biomarker, a second fluorescence tag is associated with the second biomarker, a third fluorescence tag is associated with a third biomarker, and a fourth fluorescence tag is associated with a fourth biomarker. In some embodiments, the first biomarker comprises a tumor and non-tumor marker. In some embodiments, the second biomarker comprises a non-tumor marker. In some embodiments, the first biomarker comprises a tumor and non-tumor marker, and the second biomarker comprises a non-tumor marker. In some embodiments, the third biomarker is expressed by all cells. In some embodiments, the fourth biomarker is expressed only in tumor cells. In some embodiments, the third biomarker is expressed by all cells and the fourth biomarker is expressed only in tumor cells. In some embodiments, one or more fluorescence tags comprise a fluorophore conjugated to an antibody having a binding affinity for a specific biomarker or another antibody. In some embodiments, one or more fluorescence tags are fluorophores with affinity for a specific biomarker.

Examples of fluorophores include, but are not limited to, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight® 350, DyLight® 405, DyLight® 488, DyLight® 549, DyLight® 594, DyLight® 633, DyLight® 649, DyLight® 680, DyLight® 750, DyLight® 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 630/650, BODIPY® 650/665, BODIPY® R6G, BODIPY® TMR, BODIPY® TR, OPAL™ 520, OPAL™ 540, OPAL™ 570, OPAL™ 620, OPAL™ 650, OPAL™ 690, and combinations thereof. In some embodiments, the fluorophore is selected from the group consisting of DAPI, Cy® 2, Cy® 3, Cy® 3.5, Cy® 5, Cy® 7, FITC, TRITC, a 488 dye, a 555 dye, a 594 dye, Texas Red, and Coumarin. Examples of a 488 dye include, but are not limited to, Alexa Fluor® 488, DyLight® 488, and CF™ 488A. Examples of a 555 dye include, but are not limited to, Alexa Fluor® 555. Examples of a 594 dye include, but are not limited to, Alexa Fluor® 594.

As used herein, a "field of view" refers to a section of a whole-slide digital image of a tissue sample. In some embodiments, the whole-slide image has 2-200 predetermined fields of view. In some embodiments, the whole-slide image has 10-200 predetermined fields of view. In some embodiments, the whole-slide image has 30-200 predetermined fields of view. In some embodiments, the whole-slide image has 10-150 predetermined fields of view. In some embodiments, the whole-slide image has 10-100 predetermined fields of view. In some embodiments, the whole-slide image has 10-50 predetermined fields of view. In some embodiments, the whole-slide image has 10-40 predetermined fields of view. In some embodiments, the whole-slide image has 10, 15, 20, 25, 30, 35, 40, 45, 50, 55, 60, 65, 70, 75, 80, 85, 90, 95, or 100, including increments therein, predetermined fields of view.

In some embodiments, the fluorescence signals attributable to the first biomarker are dilated by a margin ranging from about 1 to about 100 pixels. In some embodiments, the margin is from about 5 to about 100 pixels. In some embodiments, the margin is from about 5 to about 90 pixels. In some embodiments, the margin is from about 5 to about 80 pixels. In some embodiments, the margin is from about 5 to about 70 pixels. In some embodiments, the margin is from about 5 to about 60 pixels. In some embodiments, the margin is from about 5 to about 50 pixels. In some embodiments, the margin is from about 5 to about 40 pixels. In some embodiments, the margin is from about 5 to about 30 pixels. In some embodiments, the margin is from about 10 to about 100 pixels. In some embodiments, the margin is from about 10 to about 90 pixels. In some embodiments, the margin is from about 10 to about 80 pixels. In some embodiments, the margin is from about 10 to about 70 pixels. In some embodiments, the margin is from about 10 to about 60 pixels. In some embodiments, the margin is from about 10 to about 50 pixels. In some embodiments, the margin is from about 10 to about 40 pixels. In some embodiments, the margin is from about 10 to about 30 pixels. In some embodiments, the margin is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 pixels. In some embodiments, a pixel is 0.5 µm wide.

In some embodiments, dilating fluorescence signals attributable to the first biomarker encompasses proximally located cells expressing the second biomarker within about 0.5 µm to about 50 µm of a plasma membrane of the cells that express the first biomarker. In some embodiments, dilating fluorescence signals attributable to the first biomarker encompasses proximally located cells expressing the second biomarker within about 2.5 µm to about 50 µm of a plasma membrane of the cells that express the first biomarker. In some embodiments, dilating fluorescence signals attributable to the first biomarker encompasses proximally located cells expressing the second biomarker within about 2.5 µm to about 45 µm of a plasma membrane of the cells that express the first biomarker. In some embodiments, dilating fluorescence signals attributable to the first biomarker encompasses proximally located cells expressing the second biomarker within about 2.5 µm to about 40 µm of a plasma membrane of the cells that express the first biomarker. In some embodiments, dilating fluorescence signals attributable to the first biomarker encompasses proximally located cells expressing the second biomarker within about 2.5 µm to about 35 µm of a plasma membrane of the cells that express the first biomarker. In some embodiments, dilating fluorescence signals attributable to the first biomarker encompasses proximally located cells expressing the second biomarker within about 2.5 µm to about 30 µm of a plasma membrane of the cells that express the first biomarker. In some embodiments, dilating fluorescence signals attributable to the first biomarker encompasses proximally located cells expressing the second biomarker within about 2.5 µm to about 25 µm of a plasma membrane of the cells that express the first biomarker. In some embodiments, dilating fluorescence signals attributable to the first biomarker encompasses proximally located cells expressing the second biomarker within about 2.5 µm to about 20 µm of a plasma membrane of the cells that express the first biomarker. In some embodiments, dilating fluorescence signals attributable to the first biomarker encompasses proximally located cells expressing the second biomarker within about 2.5 µm to about 15 µm of a plasma membrane of the cells that express the first biomarker. In some embodiments, dilating fluorescence signals attributable to the first biomarker encompasses proximally located cells expressing the second biomarker within about 5 µm to about 50 µm of a plasma membrane of the cells that express the first biomarker. In some embodiments, dilating fluorescence signals attributable to the first biomarker encompasses proximally located cells expressing the second biomarker within about 5 µm to about 45 µm of a plasma membrane of the cells that express the first biomarker. In some embodiments, dilating fluorescence signals attributable to the first biomarker encompasses proximally located cells expressing the second biomarker within about 5 µm to about 40 µm of a plasma membrane of the cells that express the first biomarker. In some embodiments, dilating fluorescence signals attributable to the first biomarker encompasses proximally located cells expressing the second biomarker within about 5 µm to about 35 μm of a plasma membrane of the cells that express the first biomarker. In some embodiments, dilating fluorescence signals attributable to the first biomarker encompasses proximally located cells expressing the second biomarker within about 5 μm to about 30 μm of a plasma membrane of the cells that express the first biomarker. In some embodiments, dilating fluorescence signals attributable to the first biomarker encompasses proximally located cells expressing the second biomarker within about 5 μm to about 25 μm of a plasma membrane of the cells that express the first biomarker. In some embodiments, dilating fluorescence signals attributable to the first biomarker encompasses proximally located cells expressing the second biomarker within about 5 μm to about 20 μm of a plasma membrane of the cells that express the first biomarker. In some embodiments, dilating fluorescence signals attributable to the first biomarker encompasses proximally located cells expressing the second biomarker within about 5 μm to about 15 μm of a plasma membrane of the cells that express the first biomarker. In some embodiments, dilating fluorescence signals attributable to the first biomarker encompasses proximally located cells expressing the second biomarker within about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm of a plasma membrane of the cells that express the first biomarker. In some embodiments, the second biomarker on the proximally located cells is in direct contact with the first biomarker.

In some embodiments, the first total area for all cells from each of the selected fields of view, which express the second biomarker, is measured in pixels.

In some embodiments, the normalization factor is a second total area for all non-tumor cells from each of the selected fields of view. In some embodiments, the second total area is measured in pixels. In some embodiments, both the first total area and the second total area measured in pixels.

In some embodiments, the normalization factor is a second total area for all cells from each of the selected fields of view which have the capacity to express the second biomarker. In some embodiments, the second total area is measured in pixels. In some embodiments, both the first total area and the second total area measured in pixels.

In some embodiments, the normalization factor is a second total area for all cells from each of the selected fields of view. In some embodiments, the second total area is measured in pixels. In some embodiments, both the first total area and the second total area measured in pixels.

In some embodiments, the threshold score is about 500 to about 5000. In some embodiments, the threshold score is about 500 to about 4500. In some embodiments, the threshold score is about 500 to about 4000. In some embodiments, the threshold score is about 500 to about 3500. In some embodiments, the threshold score is about 500 to about 3000. In some embodiments, the threshold score is about 500 to about 2500. In some embodiments, the threshold score is about 500 to about 2000. In some embodiments, the threshold score is about 500 to about 1500. In some embodiments, the threshold score is about 500 to about 1000. In some embodiments, the threshold score is about 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, including increments therein. In some embodiments, the threshold score is about 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, including increments therein, plus or minus 100.

In some embodiments, the predetermined factor is from about 10 to about $10^5$. In some embodiments, the predetermined factor is from about $10^2$ to about $10^5$. In some embodiments, the predetermined factor is from about $10^3$ to about $10^5$. In some embodiments, the predetermined factor is from about $10^4$ to about $10^5$. In some embodiments, the predetermined factor is about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000, 70000, 80000, 90000, or $10^5$, including increments therein.

In some embodiments, the predictive power is quantified as a positive predictive value, a negative predictive value, or a combination thereof. A positive predictive value is calculated by dividing the number of patients who respond to treatment with scores above the threshold score by the total number of patients who respond to treatment. A negative predictive value is calculated by dividing the number of patients who do not respond to treatment with scores below the threshold score by the total number of patients who do not respond to treatment.

In some embodiments, the positive predictive value is greater than 60%. In some embodiments, the positive predictive value is 65% or greater. In some embodiments, the positive predictive value is 70% or greater. In some embodiments, the positive predictive value is 75% or greater. In some embodiments, the positive predictive value is 80% or greater. In some embodiments, the positive predictive value is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, including increments therein.

In some embodiments, the negative predictive value is 60% or greater. In some embodiments, the negative predictive value is 65% or greater. In some embodiments, the negative predictive value is 70% or greater. In some embodiments, the negative predictive value is 75% or greater. In some embodiments, the negative predictive value is 80% or greater. In some embodiments, the negative predictive value is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, including increments therein.

In methods disclosed herein, the cancer patient is a mammal. In some embodiments, the mammal is human. In some embodiments, the mammal is not human. In further embodiments, the mammal is mouse, rat, guinea pig, dog, cat, or horse.

In methods disclosed herein, tumor tissue is taken from a cancer patient. The type of cancer includes, but is not limited to, cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites, or a combination of one or more thereof.

Examples of immunotherapy include, but are not limited to, monoclonal antibodies (e.g., alemtuzumab or trastuzumab), conjugated monoclonal antibodies (e.g., ibritumomab tiuxetan, brentuximab vendotin, or ado-trastuzumab emtansine), bispecific monoclonal antibodies (blinatumomab), immune checkpoint inhibitors (e.g., ipilimumab, pembrolizumab, nivolumab, atezolizumab, or durvalumab), thalidomide, lenalidomide, pomalidomide, and imiquimod, and combinations thereof. In some embodiments, the immunotherapy comprises immune checkpoint therapy.

In another aspect, disclosed herein are methods of determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first specific biomarker relative to other fields of view; (ii) for each of the selected fields of view, dilating fluorescence signals attributable to the first specific biomarker to encompass proximally located cells expressing a second specific biomarker; and (iii) dividing a first total area for all cells from each of the selected fields of view, which express the second specific biomarker and are encompassed within the dilated fluorescence signals attributable to the cells expressing the first specific biomarker, with a normalization score, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein methods of determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker to encompass cells expressing a second biomarker within about 0.5 μm to about 50 μm of a plasma membrane of the cells that express the first biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein methods of determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker by a margin ranging from about 1 to about 100 pixels to encompass proximally located cells expressing a second biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein methods of determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker by a margin ranging from about 1 to about 100 pixels to encompass cells expressing a second biomarker within about 0.5 µm to about 50 µm of a plasma membrane of the cells that express the first biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In some embodiments, the spatial proximity score (SPS) is determined by the following equation:

$$SPS = \frac{A_I}{A_{NT}} \times 10^4$$

wherein $A_I$ is a total interaction area (total area of cells expressing the second specific biomarker and encompassed by dilated fluorescence signals attributable to cells expressing the first specific biomarker) and $A_{NT}$ is the total area of non-tumor cells.

In some embodiments, the spatial proximity score is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker.

In another aspect, methods of scoring a sample comprising tumor tissue from a cancer patient are used in methods of treating cancer in the patient. In some embodiments, the methods of scoring a sample comprising tumor tissue from a cancer patient are performed prior to administration of immunotherapy.

In some embodiments, disclosed herein are methods of treating cancer in a patient in need thereof, the method comprising: (a) scoring a sample comprising tumor tissue taken from the patient comprising (i) using the sample comprising tumor tissue taken from the patient, determining a score representative of a spatial proximity between at least one pair of cells, a first member of the at least one pair of cells expressing a first biomarker and a second member of the at least one pair of cells expressing a second biomarker that is different from the first biomarker; and (ii) recording the score; (b) comparing the score to a threshold value; and (b) administering immunotherapy to the patient if the score when compared to the threshold value is indicative of a likelihood that the patient will respond positively to the immunotherapy. In some embodiments, the determining step is as described herein.

Figure 14:
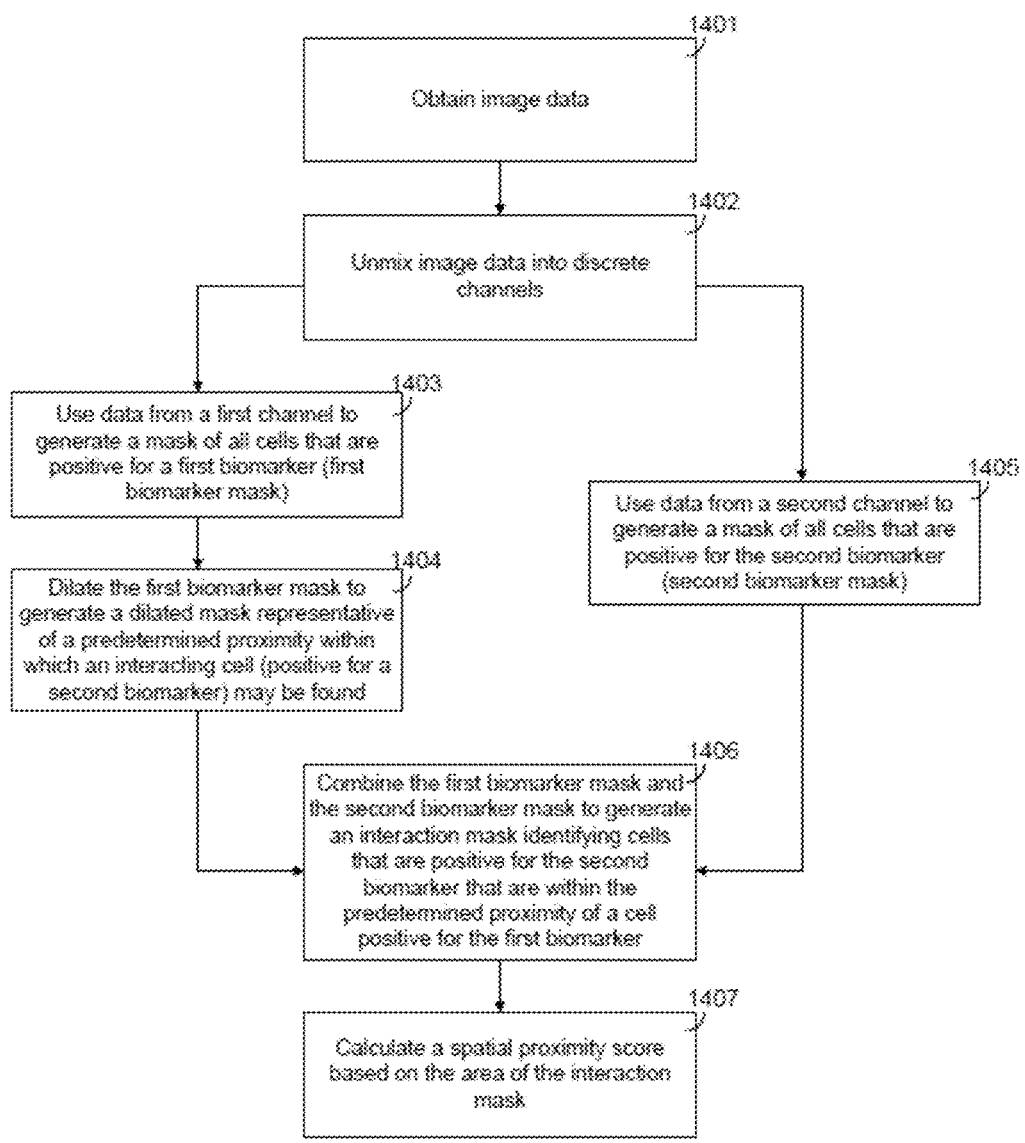
FIG. 14 is a flowchart of a process for scoring a sample comprising tumor tissue, according to an exemplary embodiment.

FIG. 14 is a flowchart depicting the steps of one embodiment of a method for scoring a sample comprising tumor tissue taken from a cancer patient. In step 1401, image data is obtained and in step 1402, the image data is unmixed such that data specific to various types of fluorescence signals are separated into different channels. In step 1403, data from a first channel is used to generate a mask of all cells that are positive for a first biomarker (first biomarker mask). The mask of all cells is then dilated (step 1404) to generate a dilated mask representative of a predetermined proximity within which an interacting cell (positive for a second biomarker) may be found. In some embodiments, the first biomarker mask is dilated between 1 and 100 pixels. In step 1405, data from a second channel is used to generate a mask of all cells that are positive for the second biomarker (second biomarker mask). In step 1406, the first biomarker mask and the second biomarker mask are combined to generate an interaction mask identifying cells that are positive for the second biomarker that are within the predetermined proximity of a cell positive for the first biomarker. In step 1407, a spatial proximity score is calculated based on the area of the interaction mask.

Figure 15:
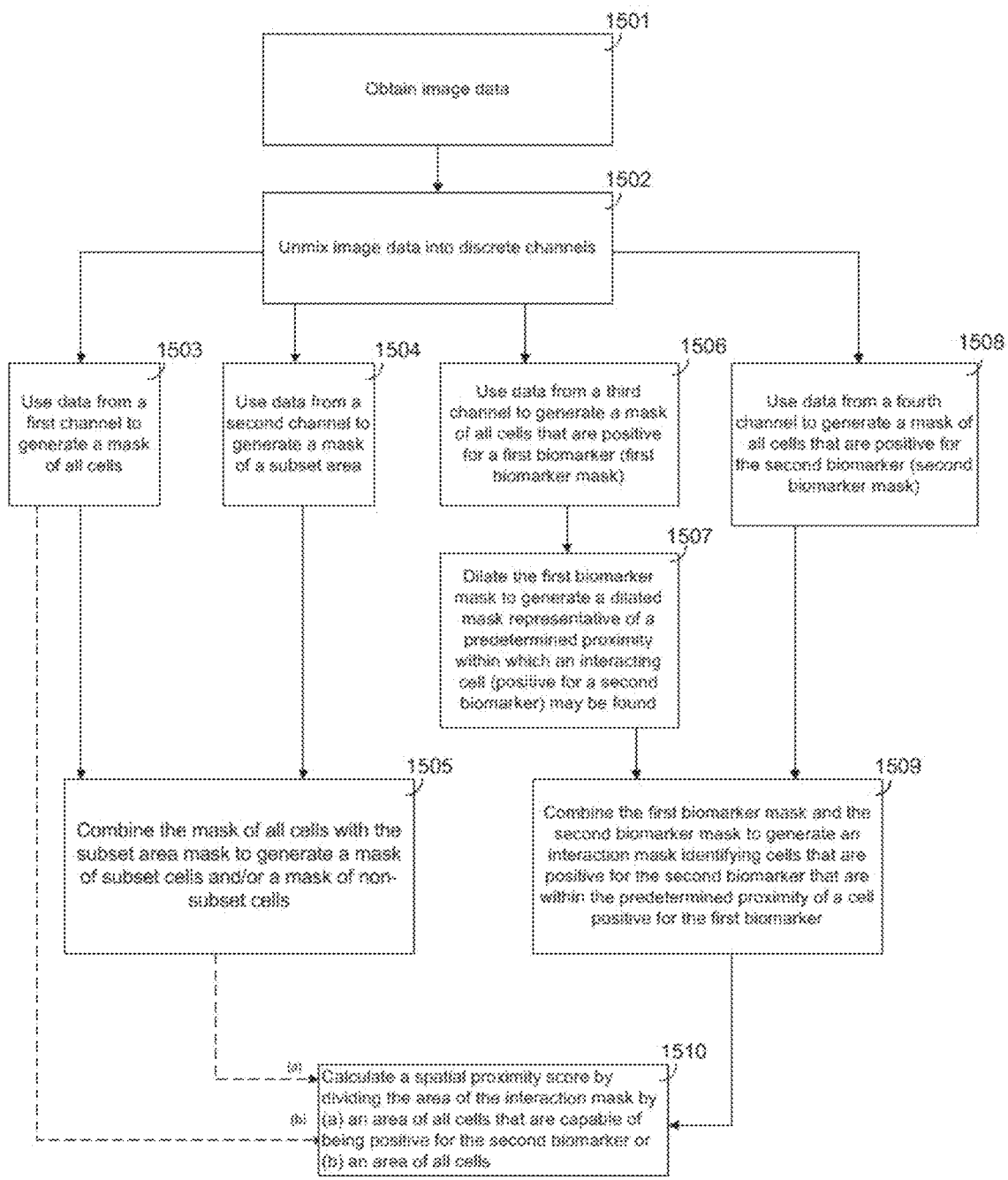
FIG. 15 is a flowchart of a process for scoring a sample comprising tumor tissue, according to a second exemplary embodiment.

FIG. 15 is a second flowchart depicting the steps of a second embodiment of a method for scoring sample comprising tumor tissue taken from a cancer patient. In step 1501, image data is obtained and in step 1502, the image data is unmixed such that data specific to various types of fluorescence signals are separated into different channels. In step 1503, data from a first channel is used to generate a mask of all cells in the field of view and in step 1504 data from a second channel is used to generate a mask of a subset area, such as tumor area, in the field of view. In step 1505 the mask of all cells is combined with the subset area mask to generate a mask of subset cells and a mask of non-subset cells. In some embodiments, the subset cells are tumor cells and the non-subset cells are non-tumor cells. In step 1506, data from a third channel is used to generate a mask of all cells that are positive for a first biomarker (first biomarker mask). The mask of all positive cells is then dilated (step 1507) to generate a dilated mask representative of a predetermined proximity within which an interacting cell (i.e., a cell that is positive for a second biomarker) may be found. In some embodiments, the first biomarker mask is dilated between 1 and 100 pixels. In step 1508, data from a fourth channel is used to generate a mask of all cells that are positive for the second biomarker (second biomarker mask). In step 1509, the dilated mask and the second biomarker mask are combined to generate an interaction mask identifying cells that are positive for the second biomarker and are within the predetermined proximity of a cell positive for the first biomarker. In step 1510, a spatial proximity score is calculated by dividing the area of the interaction mask by an area of all cells that are capable of being positive for the second biomarker (the subset cells) or by an area of all cells (as indicated by the dotted lines in the flowchart of FIG. 15 representing use of either input). In some embodiments, the cells that are capable of being positive for the second biomarker are tumor cells or non-tumor cells.

In some embodiments, a subset of cells and a non-subset of cells corresponds to tumor cells and non-tumor cells, respectively or vice versa. In some embodiments, a subset of cells and a non-subset of cells corresponds to viable cells and non-viable cells, respectively or vice versa. In some embodiments, a subset of cells is a subset of viable cells and a non-subset of cells consists of the viable cells not included in the subset of viable cells. In some embodiments, a subset of cells and a non-subset of cells corresponds to T cells and non-T cells, respectively or vice versa. In some embodiments, a subset of cells and a non-subset of cells corresponds to myeloid cells and non-myeloid cells, respectively or vice versa.

In some embodiment, the spatial proximity score is representative of a nearness of a pair of cells. In some embodiments, the nearness of a pair of cells may be determined by a proximity between the boundaries of the pair of cells, a proximity between the centers of mass of the pair of cells, using boundary logic based on a perimeter around a selected first cell of the pair of cells, determining an intersection in the boundaries of the pair of cells, and/or by determining an area of overlap of the pair of cells.

In some embodiment, the spatial proximity score is associated with metadata associated with the images of the sample, included in a generated report, provided to an operator to determine immunotherapy strategy, recorded in a database, associated with a patient's medical record, and/or displayed on a display device.

Figure 16:
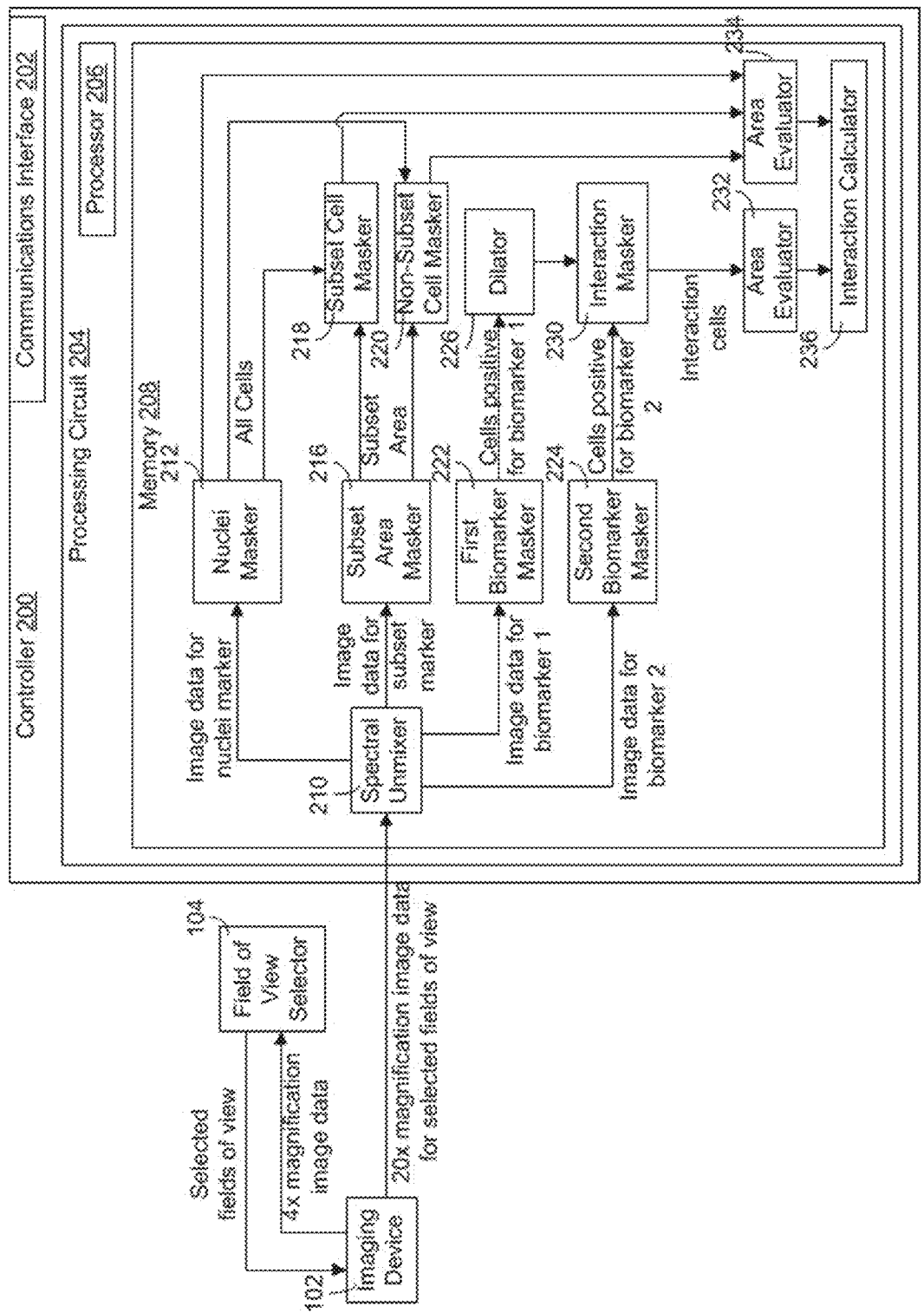
FIG. 16 is a block diagram of a controller configured to score a sample comprising tumor tissue taken from a cancer patient, according to an exemplary embodiment.

In the methods disclosed herein, the manipulation of the digital images may be carried out by a computing system comprising a controller, such as the controller illustrated in the block diagram of FIG. 16, according to an exemplary embodiment. Controller 200 is shown to include a communications interface 202 and a processing circuit 204. Communications interface 202 may include wired or wireless interfaces (e.g., jacks, antennas, transmitters, receivers, transceivers, wire terminals, etc.) for conducting data communications with various systems, devices, or networks. For example, communications interface 202 may include an Ethernet card and port for sending and receiving data via an Ethernet-based communications network and/or a WiFi transceiver for communicating via a wireless communications network. Communications interface 202 may be configured to communicate via local area networks or wide area networks (e.g., the Internet, a building WAN, etc.) and may use a variety of communications protocols (e.g., BACnet, IP, LON, etc.).

Communications interface 202 may be a network interface configured to facilitate electronic data communications between controller 200 and various external systems or devices (e.g., imaging device 102). For example, controller 200 may receive imaging data for the selected fields of view from the imaging device 102, to analyze the data and calculate the spatial proximity score (SPS).

Still referring to FIG. 16, processing circuit 204 is shown to include a processor 206 and memory 208. Processor 206 may be a general purpose or specific purpose processor, an application specific integrated circuit (ASIC), one or more field programmable gate arrays (FPGAs), a group of processing components, or other suitable processing components. Processor 506 may be configured to execute computer code or instructions stored in memory 508 or received from other computer readable media (e.g., CDROM, network storage, a remote server, etc.).

Memory 208 may include one or more devices (e.g., memory units, memory devices, storage devices, etc.) for storing data and/or computer code for completing and/or facilitating the various processes described in the present disclosure. Memory 208 may include random access memory (RAM), read-only memory (ROM), hard drive storage, temporary storage, non-volatile memory, flash memory, optical memory, or any other suitable memory for storing software objects and/or computer instructions. Memory 208 may include database components, object code components, script components, or any other type of information structure for supporting the various activities and information structures described in the present disclosure. Memory 508 may be communicably connected to processor 206 via processing circuit 204 and may include computer code for executing (e.g., by processor 206) one or more processes described herein.

Still referring to FIG. 16, controller 200 is shown to receive input from an imaging device 102. The imaging device acquires all of the imaging data and records it, along with all of the meta-data which describes it. The imaging device will then serialize the data into a stream which can be read by controller 200. The data stream may accommodate any binary data stream type such as the file system, a RDBM or direct TCP/IP communications. For use of the data stream, controller 200 is shown to include a spectral unmixer 210. The spectral unmixer 210 may receive image data from an imaging device 102 on which it performs spectral unmixing to unmix an image presenting various wavelengths into individual, discrete channels for each band of wavelengths. For example, the image data may be "unmixed" into separate channels for each of the various fluorophores used to identify cells or proteins of interest in the tissue sample. The fluorophore, by way of example only, may be one or more of the group consisting of DAPI, Cy® 2, Cy® 3, Cy® 3.5, Cy® 5, FITC, TRITC, a 488 dye, a 555 dye, a 594 dye, and Texas Red. In one example, one of the channels may include image data that falls within a predetermined band surrounding a wavelength of 461 nm (the maximum emission wavelength for DAPI), to identify nuclei in the image. Other channels may include image data for different wavelengths to identify different portions of the tissue sample using different fluorophores.

Controller 200 is also shown to include various maskers, such as cell masker 212, subset area masker 216, first biomarker masker 22, and second biomarker masker 224. These, or other maskers that may be included in the controller 200 in other embodiments, are used to receive an unmixed signal from the spectral unmixer 210 and create a mask for the particular cell or area of interest, dependent on the fluorophore used to identify certain features of interest in the tissue sample. To create a mask, the maskers (such as cell masker 212, subset area masker 216, first biomarker masker 22, and second biomarker masker 224) receive image data related to an intensity of each pixel in the field of view. Pixel intensity is directly proportional to the amount of fluorescence emitted by the sample, which in turn, is directly proportional to the amount of protein biomarker in the sample (when using a fluorophore to identify a particular biomarker). An absolute threshold may be set based on the values which exist in the image pixels. All the pixels which are greater than or equal to the threshold value will be mapped to 1.0, or "on", and all other pixels will be mapped to 0.0, or "off." In this way, a binary mask is created to identify the cell or tissue portion of interest in the field of view. In other embodiments, a mask is created using a lower bound wherein all pixels with an intensity at or above a lower bound are accepted and used as the pixel value for the mask. If the intensity is below the lower bound, the pixel value is set to 0.0, or "off".

Figure 17:
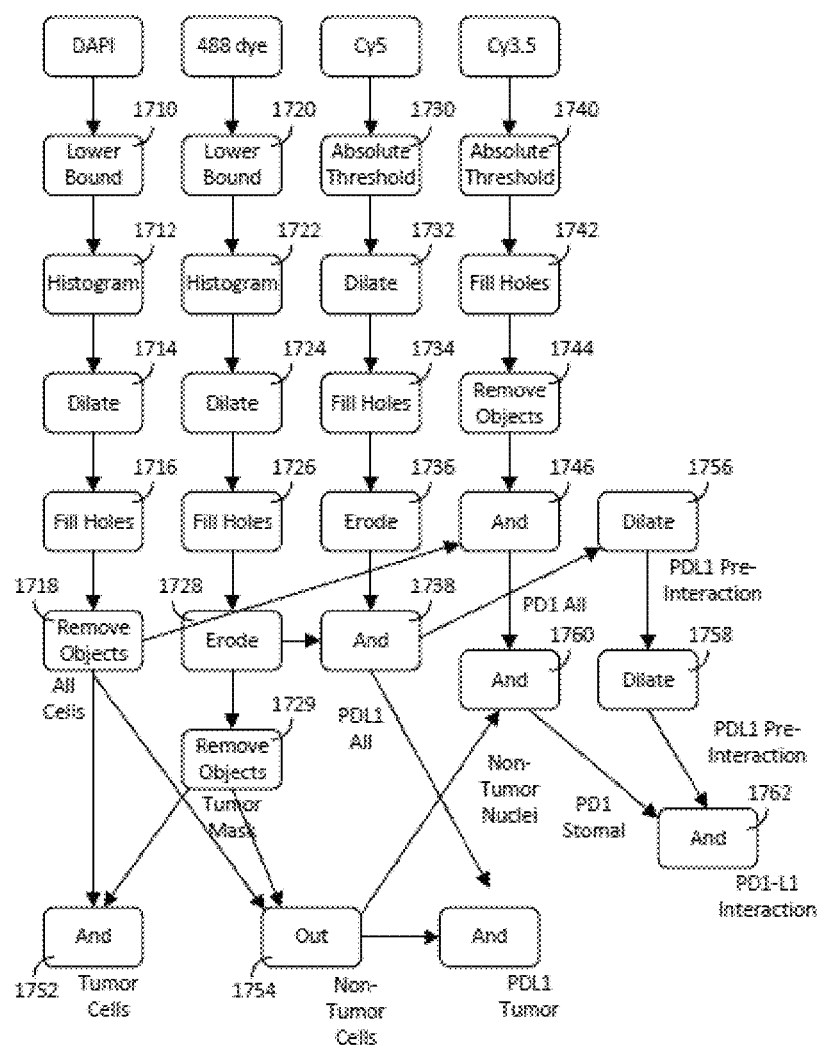
FIG. 17 is a flow diagram of the image processing steps used to score a sample comprising tumor tissue, according to an exemplary embodiment.

In the example flow diagram for masking shown in FIG. 17, it is shown that the DAPI and 488 channels (for identifying nuclei and tumor areas, respectively) use the lower bound protocol (steps 1710, 1712, 1720, 1722), while Cy5 and Cy3.5 channels (for identifying biomarkers) use a threshold value protocol (steps 1730, 1740), for providing the mask outputs. In association with the lower bound protocol, there is also a histogram step to determine the lower bound. In particular, histogram threshold (step 1712, 1722) produces a threshold of an input image but uses a sliding scale to determine the point at which the thresholding occurs. The inputs are the current image and a user defined threshold percentage. The latter is used to determine at what percent of the total intensity the threshold level should be set. Firstly, the intensity of every pixel is summed into a total intensity. The threshold percentage is multiplied by this total intensity to obtain a cut-off sum. Finally, all pixels are grouped by intensity (in a histogram) and their intensities summed from lowest to highest (bin by bin) until the cut-off sum is achieved. The last highest pixel intensity visited in the process is the threshold for the current image. All pixels with intensities greater than that value have their intensities set to maximum while all others are set to the minimum.

The steps identified as steps 1714, 1716, 1724, 1726, 1728, 1732, 1734, 1736, 1742, 1744 in FIG. 17 represent intermediary steps that occur in the initial maskers, such as cell masker 212, subset area masker 216, first biomarker masker 222, and second biomarker masker 224. These steps are defined as follows:

Dilate increases the area of brightest regions in an image. Two inputs are need for dilate. The first is the implicit current image and the second is the number of iterations to dilate. It is assumed that only binary images are used for the first input. The procedure will operate on continuous images, but the output will not be a valid dilate. The dilate process begins by first finding the maximum pixel intensity in the image. Subsequently, each pixel in the image is examined once. If the pixel under investigation has intensity equal to the maximum intensity, that pixel will be drawn in the output image as a circle with iterations radius and centered on the original pixel. All pixels in that circle will have intensity equal to the maximum intensity. All other pixels are copied into the output image without modification.

The fill holes procedure will fill "empty" regions of an image with pixels at maximum intensity. These empty regions are those that have a minimum intensity and whose pixel area (size) is that specified by the user. The current image and size are the two inputs required. Like dilate this procedure should only be applied to binary images.

Erode processes images in the same fashion as dilate. All functionality is the same as dilate except that the first step determines the minimum intensity in the image, only pixels matching that lowest intensity are altered, and the circles used to bloom the found minimum intensity pixels are filled with the lowest intensity value. Like dilate this procedure should only be applied to binary images.

Remove Objects. Two inputs are expected: the current image and object size. Remove objects is the opposite of the fill holes procedure. Any regions containing only pixels with maximum intensity filling an area less than the input object size will be set to minimum intensity and thusly "removed." This procedure should only be applied to binary images; application to continuous images may produce unexpected results.

The output at final steps 1718, 1729, 1738, and 1746 are the resultant cell mask, subset area mask (or, in this particular example, the tumor area mask), biomarker 1 cell mask, and biomarker 2 cell mask, respectively. FIG. 17 further depicts the combinations of these resultant masks to calculate the spatial proximity score. These combinations are described below with reference to the combination maskers of the controller 200, depicted in FIG. 16.

Controller 200 is shown to include combination maskers, such as subset cell masker 218, non-subset cell masker 220, and interaction masker 230. Subset cell masker performs an And operation, as shown at step 1752 in FIG. 17, to combine the output of the cell masker 212 (representative of all cells in the image) with the output of the subset area masker 216. Accordingly, subset cell masker generates a mask of all subset cells in the image. In some embodiments, the subset cells are tumor cells. This same combination, using an Out operation performed by non-subset cell masker 220 as shown at step 1754 in FIG. 17, generates a mask of all non-subset cells in the sample image. In some embodiments, the non-subset cells are non-tumor cells.

Before being combined with another mask, the first biomarker mask (from first biomarker masker 222) is dilated by dilator 226. The dilated mask represents an area surrounding those cells expressing a first biomarker, so as to identify a space in which cells expressing the second biomarker would be within a proper proximity to interact with the cell expressing the first biomarker. This is represented by steps 1756 and 1758 of FIG. 17. The flow chart of FIG. 17 shows the dilation taking place in two steps, 1756 and 1758. This may be required when there is a limit to the maximum iterations in each step. For example, there may be a maximum of 10 iterations (corresponding to a 10 pixel increase), so when a 20 pixel increase is needed, the dilation must be split into two subsequent steps.

Within second biomarker masker 224, the biomarker mask may be combined with the non-subset cell mask described above, using an And operation, as shown in step 1760 of FIG. 17, to generate a mask of all non-subset cells that are positive for the first biomarker. This mask is then combined (step 1762) at interaction masker 230 with the dilated mask from dilator 226 to generate an interaction mask. The interaction mask identified the non-subset cells that are positive for the second biomarker and that are also within the interaction area, or that overlap the dilated mask. These identified cells, then, represent the cells that could interact with the cells positive for the first biomarker, thus resulting in greater therapy response.

To calculate the spatial proximity score (SPS), the area of the interaction mask is determined in pixels at the area evaluator 232. In some embodiments, the area of all the cells that are capable of expressing the second biomarker is determined in pixels at the area evaluator 234. The cells that are capable of expressing the second biomarker may be tumor cells or non-tumor cells. In some embodiments, In some embodiments, the area of all cells is determined in pixels at the area evaluator 234. An interaction, or spatial proximity, score is determined at the interaction calculator 236 by dividing the area from area evaluator 232 by the area from area evaluator 234 and multiplying by a predetermined factor. As described above, in one embodiment, the equation executed by the interaction calculator 236 is:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker or the total area of all cells in the field of view.

The And procedure is modeled after a binary AND operation, but differs in significant ways. And accepts the current image and a user selected resultant. The output is an image created by performing a multiplication of the normalized intensities of matching pixels from the two input images. In some cases, image intensity data is already normalized. Therefore, the And procedure is simply a pixel-wise multiplication of the two images. The two inputs required for Out are the current image and a user selected resultant. Out removes the second image form the first according to the formula $A*(1-B/B_{max})$ where A is the current image, B the user selected image to remove, and $B_{max}$ is the maximum intensity of B. Note that the division of B by $B_{max}$ normalizes B.

EXAMPLES

Example 1. Sample Preparation, Imaging, and Analysis of Imaging for Melanoma Tissue Samples from Human Patients Sample preparation. Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining.

Next, the slides were stained with a mouse anti-PD1 primary antibody. Slides were then washed before incubation with an anti-mouse HRP secondary antibody. Slides were washed and then PD-1 staining was detected using TSA+Cy® 3.5 (Perkin Elmer). Any residual HRP was then quenched using two washes of fresh 100 mM benzhydrazide with 50 mM hydrogen peroxide. The slides were again washed before staining with a rabbit anti-PD-L1 primary antibody. Slides were washed and then incubated with a cocktail of anti-rabbit HRP secondary antibody plus mouse anti-S100 directly labeled with 488 dye and 4',6-diamidino-2-phenylindole (DAPI). Slides were washed and then PD-L1 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 1. Alternatively, slides were stained with anti-CD8 primary antibody in place of anti-PD1 primary antibody.

Sample imaging and analysis. Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue), FITC (green), and Cy® 5 (red) to create RGB images. These 4× images were processed using an automated enrichment algorithm (developed using inForm) in field of view selector 104 to identify and rank possible 20× magnification fields of view according to the highest Cy® 5 expression.

The top 40 fields of view were imaged at 20× magnification across DAPI, FITC, Texas Red, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 210 into individual channels and saved as a separate file.

The processed files were further analyzed using AQUAnalysis™ or through a fully automated process using AQUAserve™. Details were as follows.

Figure 2A:
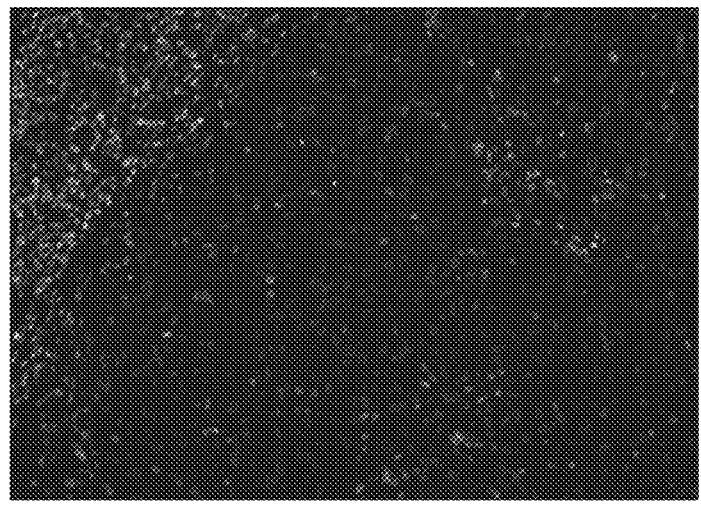
FIG. 2a shows a non-limiting example of all nuclei detected with DAPI within an image.
Figure 2B:
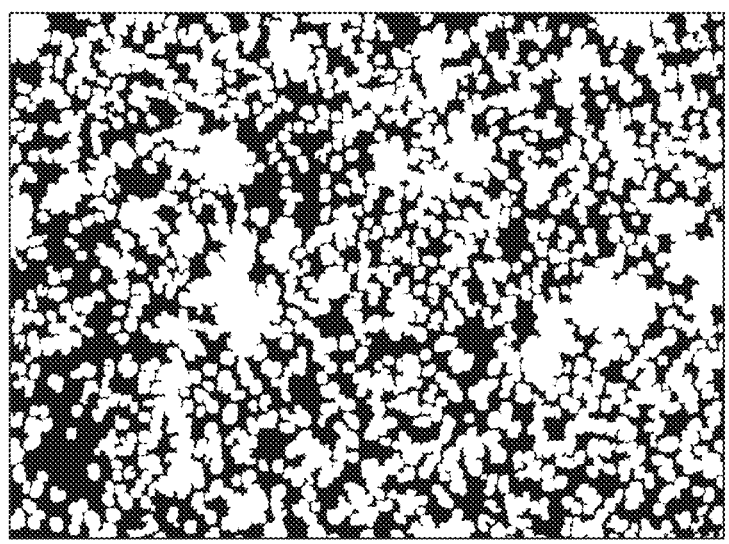

Each DAPI image was processed by nuclei masker 212 to identify all cell nuclei within that image (FIG. 2a), and then dilated by 3 pixels to represent the approximate size of an entire cell. This resulting mask represented all cells within that image (FIG. 2b).

Figure 3A:
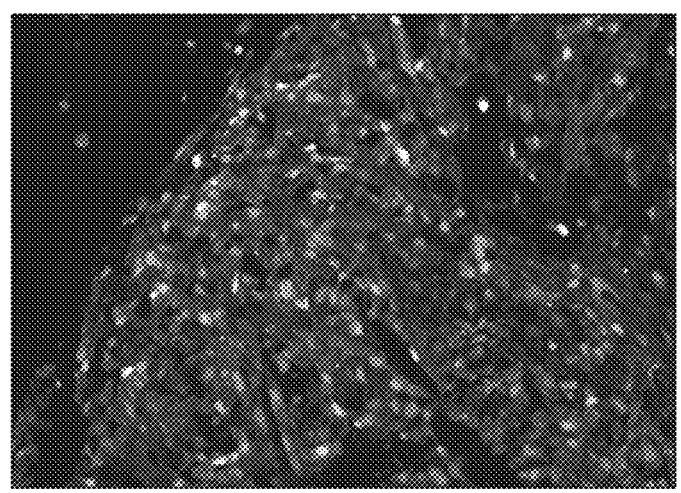
FIG. 3a shows a non-limiting example of an image of S100 detected with 488 dye.
Figure 3B:
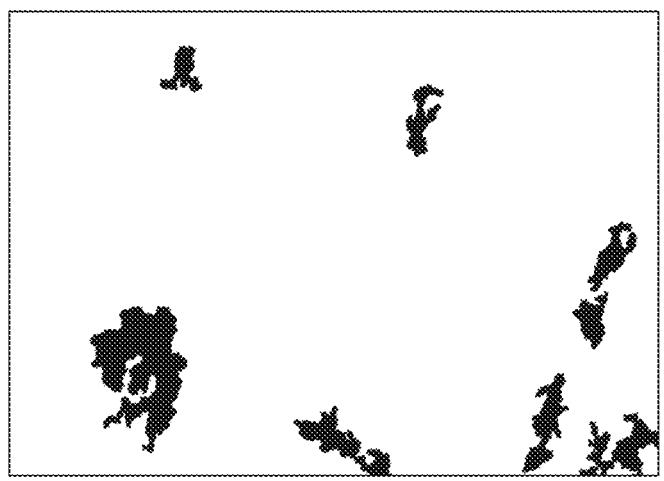
Figure 3C:
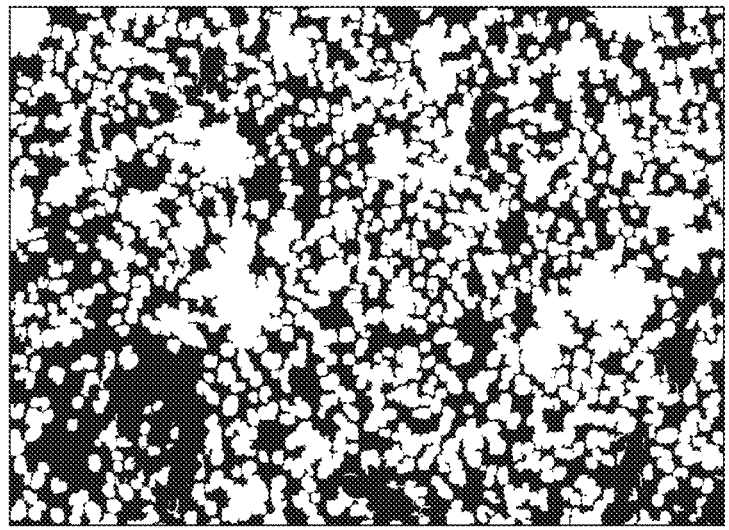

S100 (tumor cell marker for melanoma) detected with 488 dye (FIG. 3a) was processed by tumor masker 216 to create a binary mask of all tumor area within that image (FIG. 3b). Overlap between this mask and the mask of all cells created a new mask for tumor cells (FIG. 3c), using tumor cell masker 218.

Figure 3D:
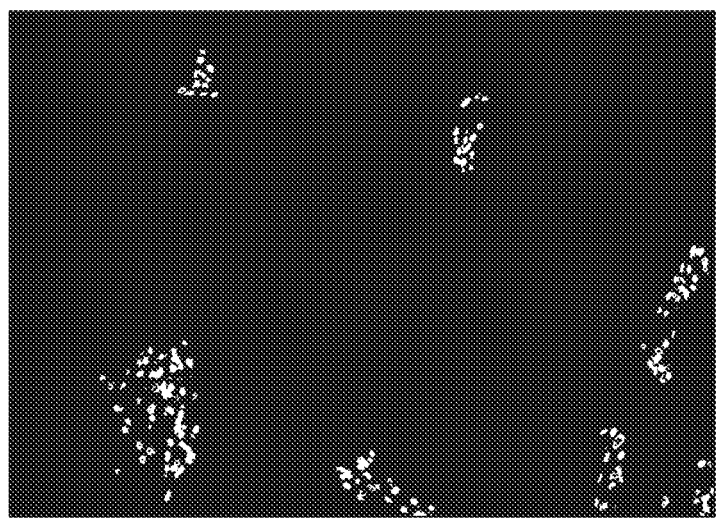

Similarly, absence of the tumor cell marker in combination with the mask of all nuclei created a new mask for all non-tumor cells (FIG. 3d), performed using non-tumor cell masker 220.

Figure 4A:
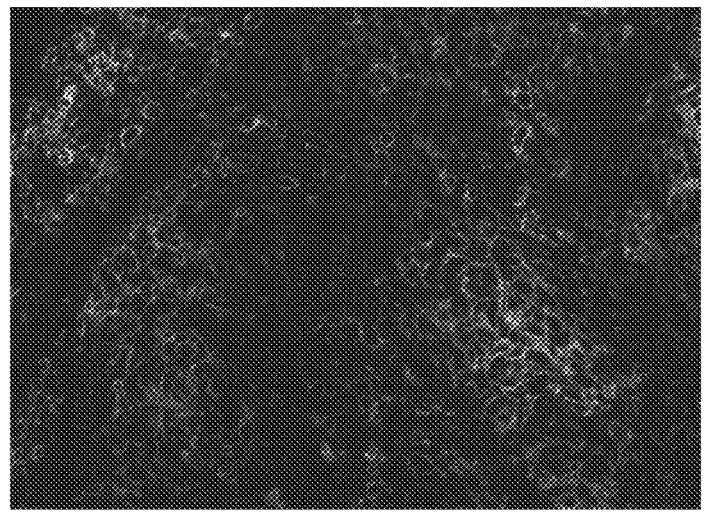
FIG. 4a shows a non-limiting example of an image of PD-L1 detected with Cy® 5.
Figure 4B:
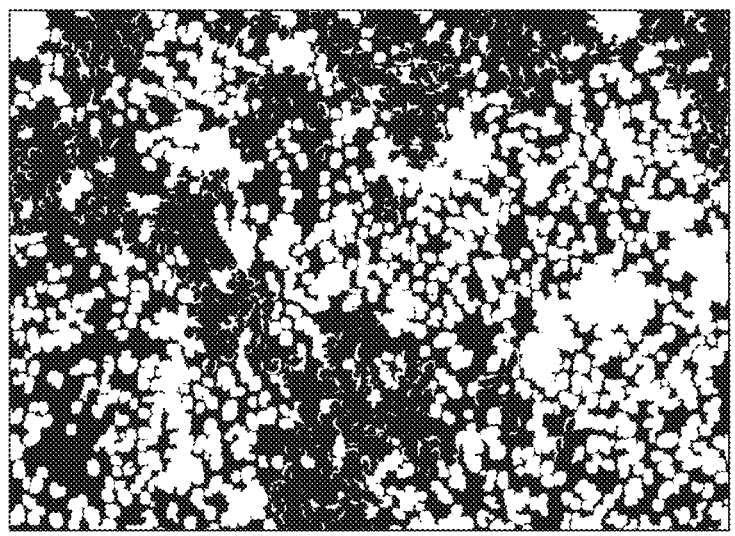

Each Cy® 5 image (FIG. 4a) was processed by first biomarker masker 222 and overlapped with the mask of all cells to create a binary mask of all cells that are PD-L1-positive (FIG. 4b). Overlapping the biomarker mask with the mask of all cells eliminated noise pixels that may be falsely identified in the mask as biomarker positive cells.

Figure 5A:
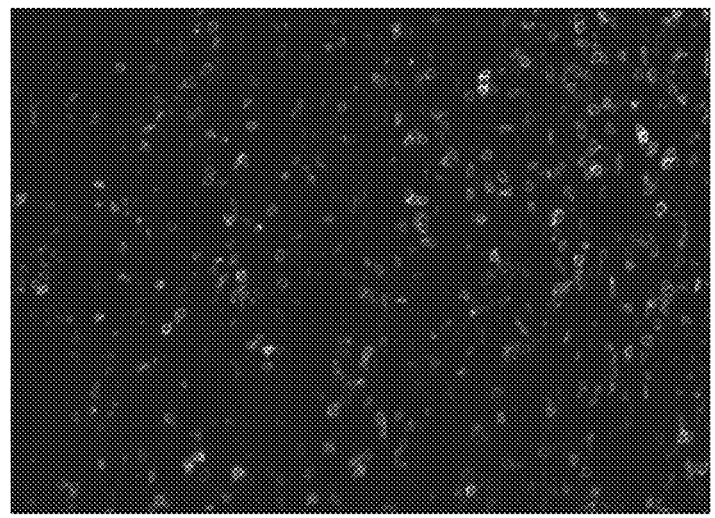
FIG. 5a shows a non-limiting example of an image of PD-1 detected with Cy® 3.5.
Figure 5B:
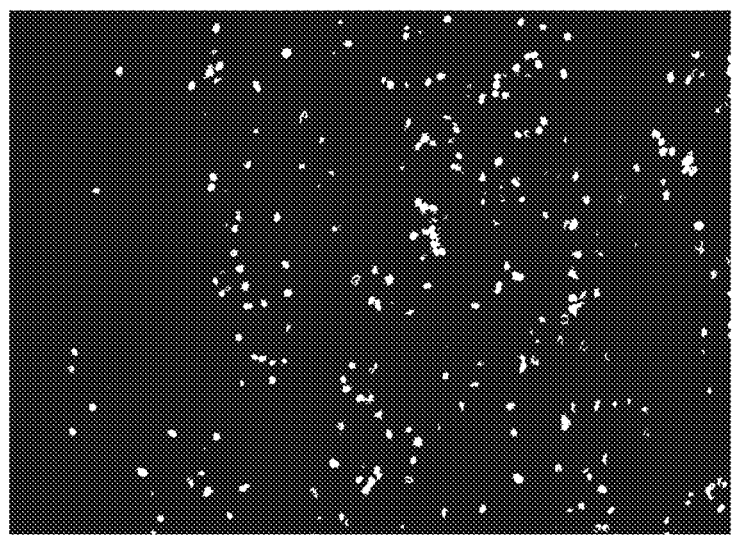

Each Cy® 3.5 image (FIG. 5a) was processed by second biomarker masker 224 to create a binary mask for PD-1-positive cells and overlapped with the mask of all non-tumor cells to create a binary mask of all non-tumor cells that are PD-1-positive (FIG. 5b). Overlapping the biomarker mask with the mask of all non-tumor cells eliminated noise pixels that may be falsely identified in the mask as biomarker positive cells.

Figure 6A:
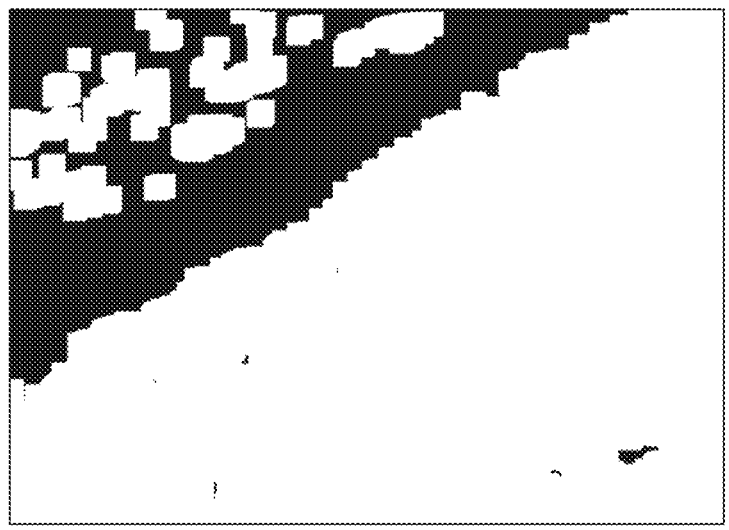
FIG. 6a shows a non-limiting example of an interaction mask of all PD-L1-positive cells and the nearest neighbor cells.
Figure 6B:
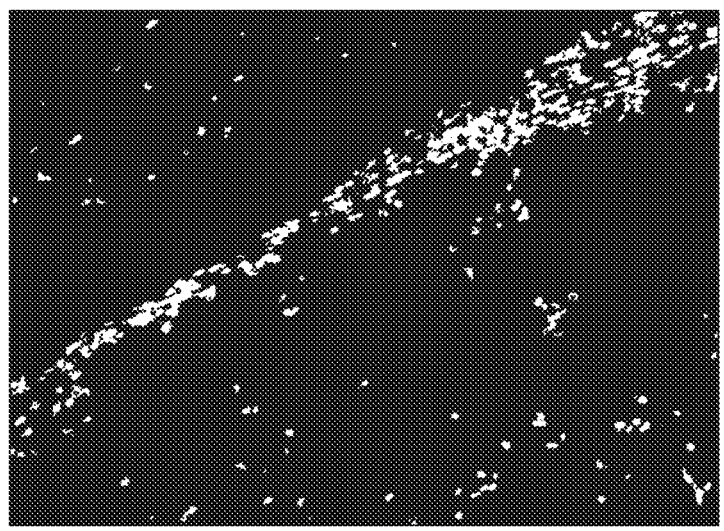
FIG. 6b shows a non-limiting example of an interaction compartment of the PD-1-positive cells in close proximity to the PD-L1-positive cells.

The binary mask of all PD-L1-positive cells was dilated using second dilator 226 to create an interaction mask encompassing the nearest neighbor cells (e.g., cells with PD-1) (FIG. 6a). This interaction mask was combined with a binary mask of all PD-1-positive non-tumor cells using interaction masker 230 to create an interaction compartment of the PD-1-positive cells in close enough proximity to the PD-L1-positive cells such that PD-1 is likely interacting with PD-L1 (FIG. 6b).

The total area from all accepted fields (up to 40 fields of view) for the interaction compartment and the total area of the non-tumor cells was calculated in area evaluators 232, 234 respectively. The total area from all accepted fields of view for the interaction compartment was divided by the total area of the non-tumor cells and multiplied by a factor of 10,000, using the interaction calculator 236 to create a whole number representing an interaction score for each specimen. PD-L1 and PD-1 measurements were highly reproducible ($R^2$=0.98 and 0.97, respectively). A broad range of PD-L1 and PD-1 expression and interaction scores were observed in archival clinical specimens (n=53). In a cohort of 26 advanced melanoma patients treated with nivolumab (n=5) or pembrolizumab (n=21), the PD-1/PD-L1 interaction score was found to reliably distinguish responders from non-responders (p=0.01) while PD-L1 alone (p=0.07) or CD8 alone (p=0.23) did not. Additionally, patients exhibiting higher PD-1/PD-L1 interaction scores had superior response rates (82% vs. 20%, p=0.01). Patients with high PD-1/PD-L1 interaction scores experienced longer median progression-free survival (p=0.059), and fewer deaths (22% vs 58%) compared with patients having lower PD-1/PD-L1 interaction scores. These results suggest that this method of scoring the tissue sample to obtain PD-1/PD-L1 interaction scores provides a superior predictive power (82% Positive Predictive Value, 80% Negative Predictive Value) compared with PD-L1 expression alone.

Figure 7A:
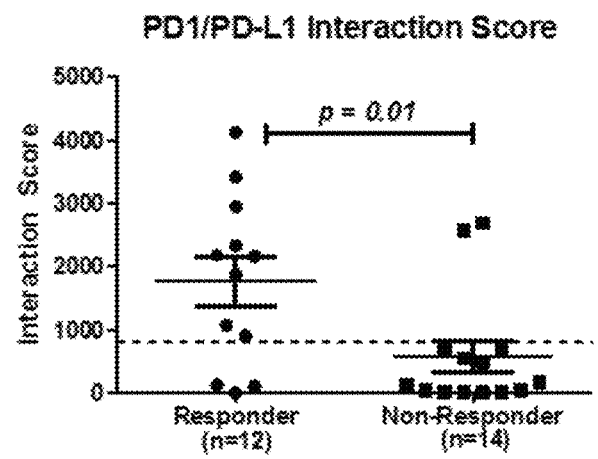
FIG. 7a shows a non-limiting example of interaction scores from 26 melanoma patients.

Representative scores from the 26 patients are shown in FIG. 7a. Based on the data, a threshold of 800-900 was selected to indicate likelihood of response to treatment.

Figure 7B:
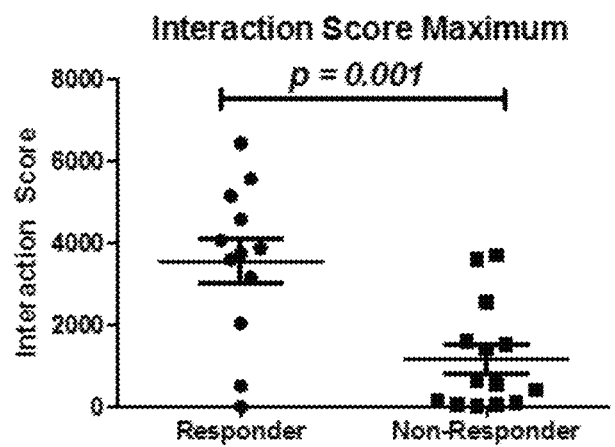

Alternatively, the interaction score was calculated for each individual field of view and the maximum score for each patient is shown in FIG. 7b. Based on the maximum score, a threshold of 1900 was selected to indicate likelihood of response to treatment.

Figure 8:
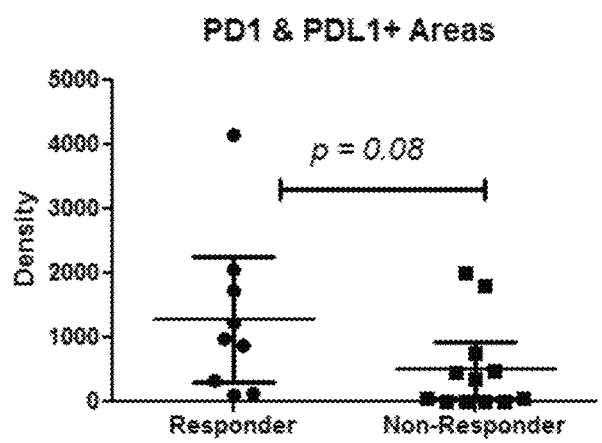
FIG. 8 shows analysis results based on whole-slide imaging in lieu of an enrichment algorithm.

To assess the effect of the enrichment algorithm on the interaction score, the above-mentioned procedures were performed using whole-slide imaging in lieu of the enrichment algorithm (see FIG. 8). When whole-slide image analysis was performed, there was no longer a statistically significant difference between the patients who responded to anti-PD1 therapy and those who did not. As such, a threshold could not be determined with this analysis.

Figure 9:
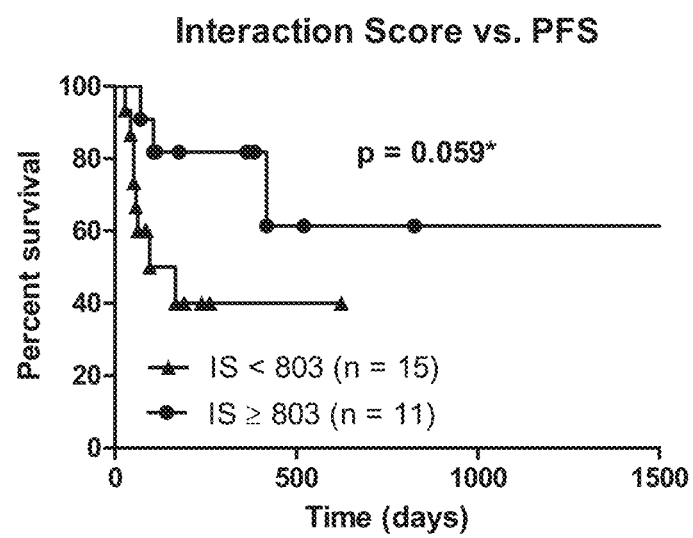
FIG. 9 shows a comparison of interaction scores with progression free survival of the 26 patients. Note: * indicates uncorrected log-rank test.
Figure 10:
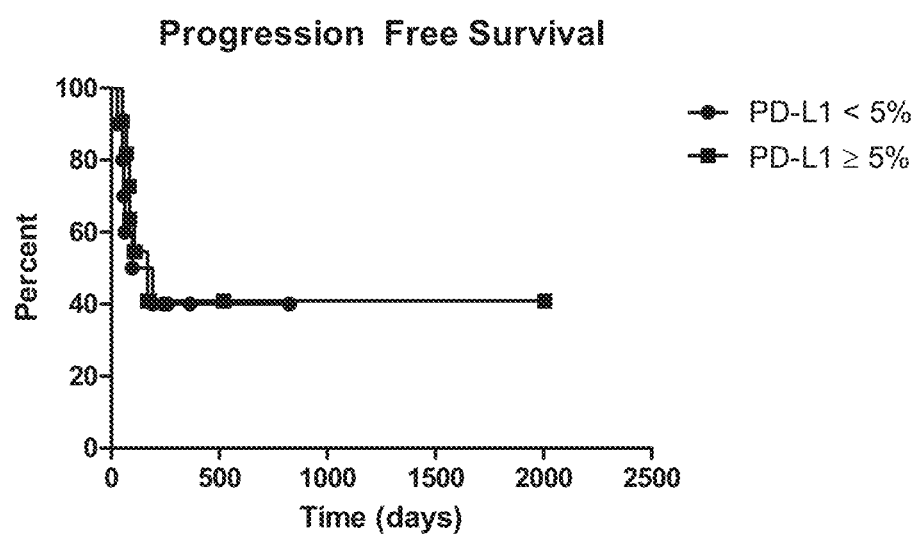
FIG. 10 shows a comparison of PD-L1 expression with progression free survival of the patients.

The interaction scores were compared with progression free survival (PFS) of the patients (FIG. 9). Interaction scores of at least 803 correlated well with survival. Notably, PD-L1 expression did not correlate with improved PFS (FIG. 10).

Figure 11:
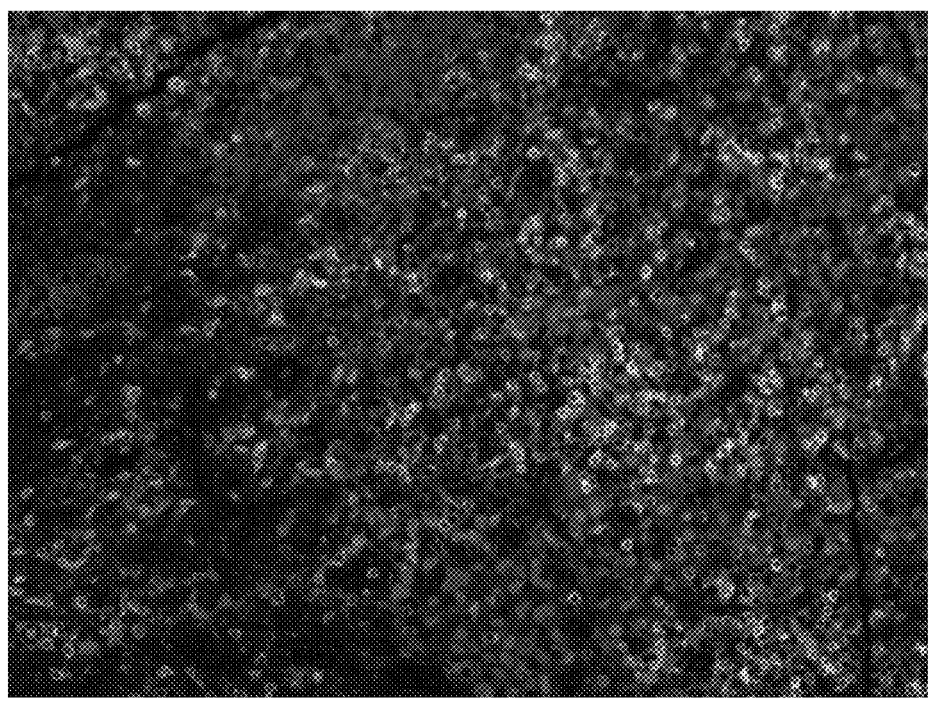
FIG. 11 shows a non-limiting example of a mask of fluorescence signals corresponding to PD-L1-positive cells (red), PD-1-positive cells (yellow), all tumor cells (green), and all cells (blue) for a positive responder to immunotherapy.
Figure 12:
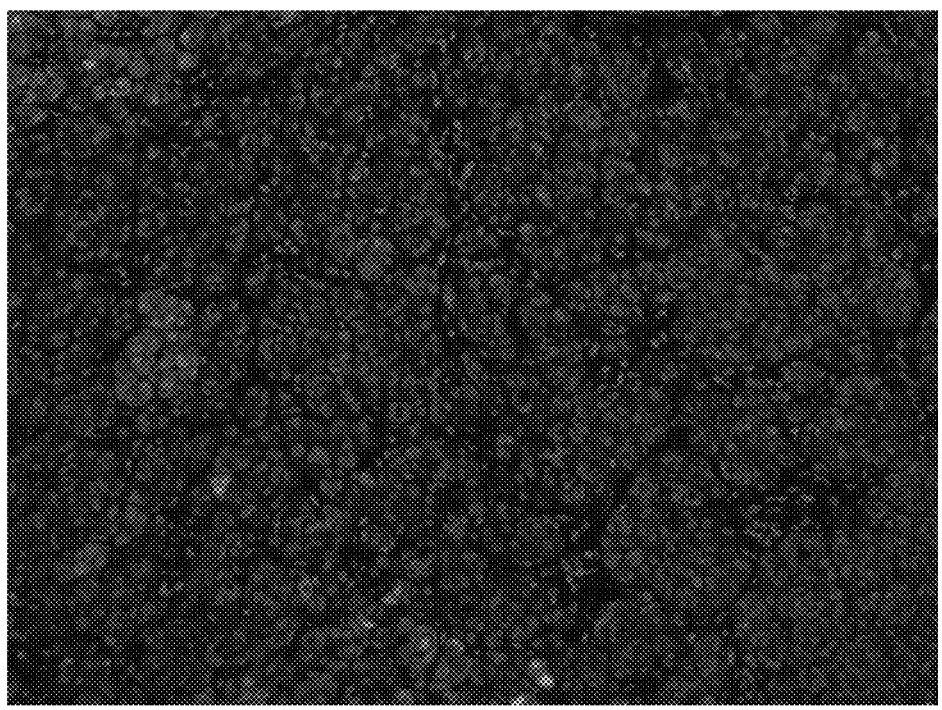
FIG. 12 shows a non-limiting example of a mask of fluorescence signals corresponding to PD-L1-positive cells (red), PD-1-positive cells (yellow), all tumor cells (green), and all cells (blue) for a negative responder to immunotherapy.

FIGS. 11 and 12 show a representative examples of overlaid masks indicating PD-L1-positive cells (red), PD-1-positive cells (yellow), tumor cells (S100, green), and all cells (DAPI, blue). For a positive responder to immunotherapy, the mask in FIG. 11 readily indicates the presence of PD-L1-positive cells (red), PD-1-positive cells (yellow), and all tumor cells (green). In contrast, for a negative responder to immunotherapy, the mask in FIG. 12 indicates the presence of tumor cells (S100, green) and all cells (DAPI, blue), but shows little to no PD-L1-positive cells (red) or PD-1-positive cells (yellow). FIG. 11 represents an interaction score of 2176 (complete response to immunotherapy). FIG. 12 represents an interaction score of 8 (no response to immunotherapy).

Figure 18:
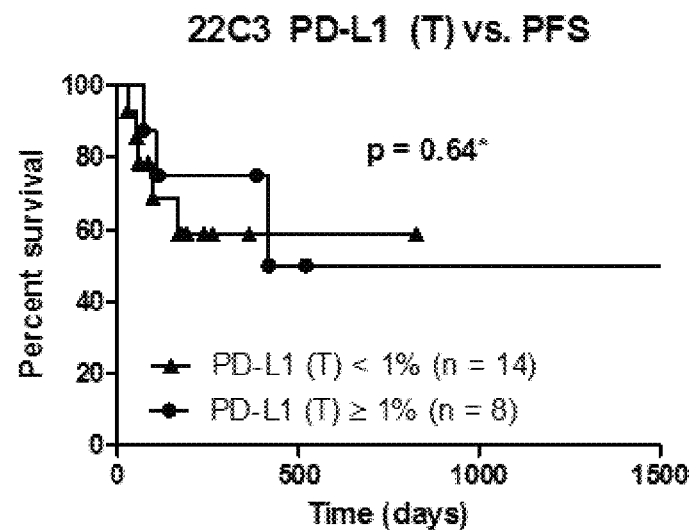
FIG. 18 shows a comparison of PD-L1 expression determined using the 22C3 FDA-approved IHC assay with progression free survival of the patients. Note: * indicates p-value was determined using uncorrected log-rank test.

The tissue samples were also assessed using an FDA-approved method to measure PD-L1 in non-small cell lung cancer with the anti-PD-L1 antibody clone 22C3, not currently used for melanoma tissue samples. PD-L1 expression was compared with patient PFS and is shown in FIG. 18. This method does not demonstrate statistically relevant diagnostic value compared to the methods described herein using interaction scores.

Figure 19A:
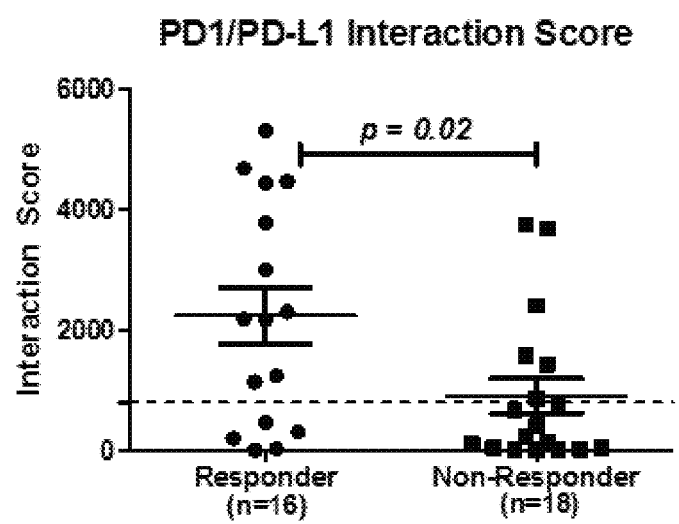
FIG. 19a shows a non-limiting example of interaction scores from 34 additional melanoma patients.
Figure 19B:
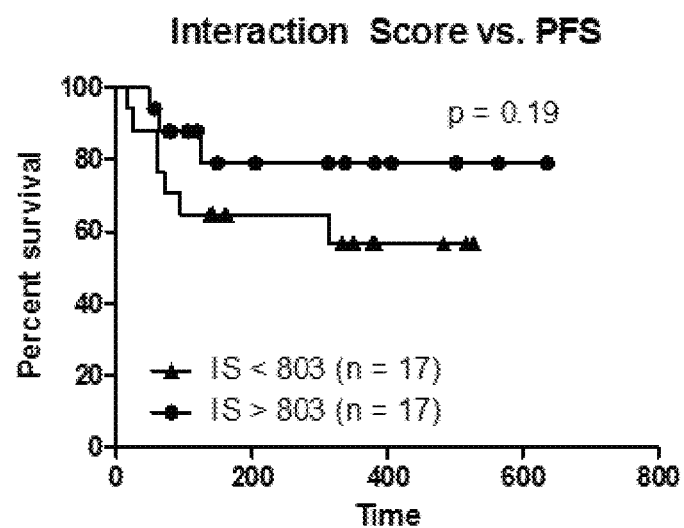

A verification cohort of 34 additional metastatic melanoma patients was examined and PD-1/PD-L1 interaction scores were obtained (see FIG. 19a). These interaction scores were also compared with progression free survival (PFS) of the patients (FIG. 19b). Although not statistically significant (p=0.19), the comparison indicates a trend of patients with higher PD-1/PD-L1 interaction scores having longer PFS. Statistical significance may be limited due to the relatively recent use of these therapies in the clinic therefore limiting the follow-up time. for these patients.

Figure 19C:
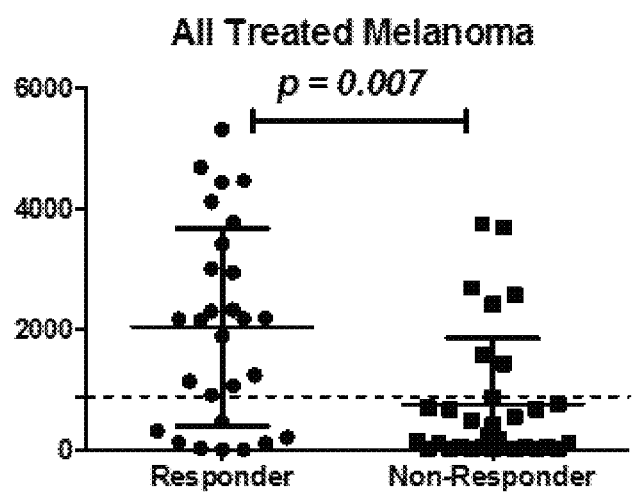
Figure 19D:
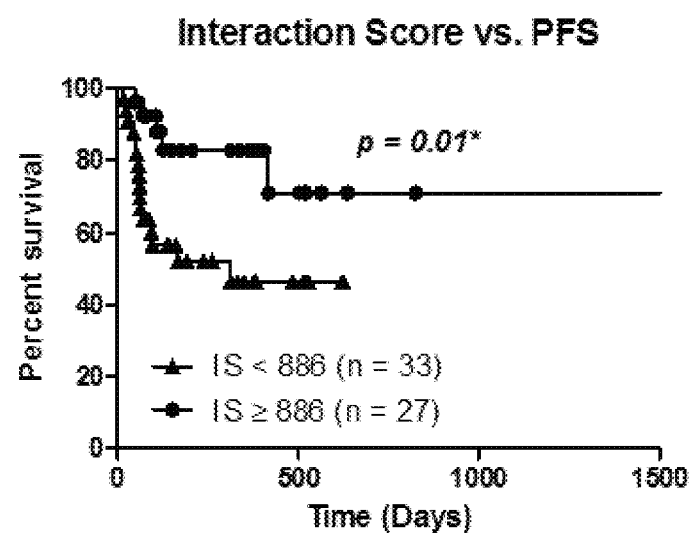
FIG. 19d shows a comparison of interaction scores with progression free survival of the patients of FIG. 19c. Note: * indicates the p-value was determined using uncorrected log-rank test.
Figure 19E:
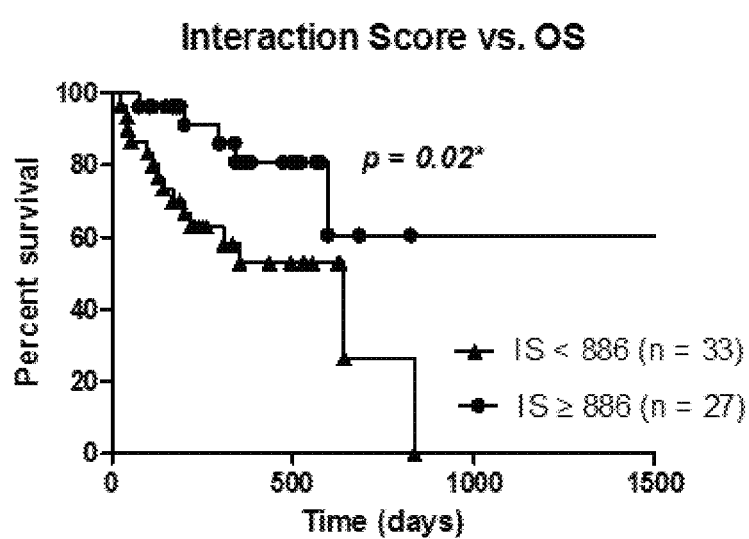
FIG. 19e shows a comparison of interaction scores with overall survival (OS) of the patients of FIG. 19c. Note: * indicates p-value was calculated using uncorrected log-rank test.

The PD-1/PD-L1 interaction scores as well as the comparison of these scores with patient PFS or patient overall survival (OS) for the combination of the earlier cohort of 26 patients with the verification cohort of 34 patients are shown in FIGS. 19c-19e. Combined analysis clearly indicate patients with high PD-1/PD-L1 demonstrate an improved response to anti-PD-1 therapies.

Figure 13:
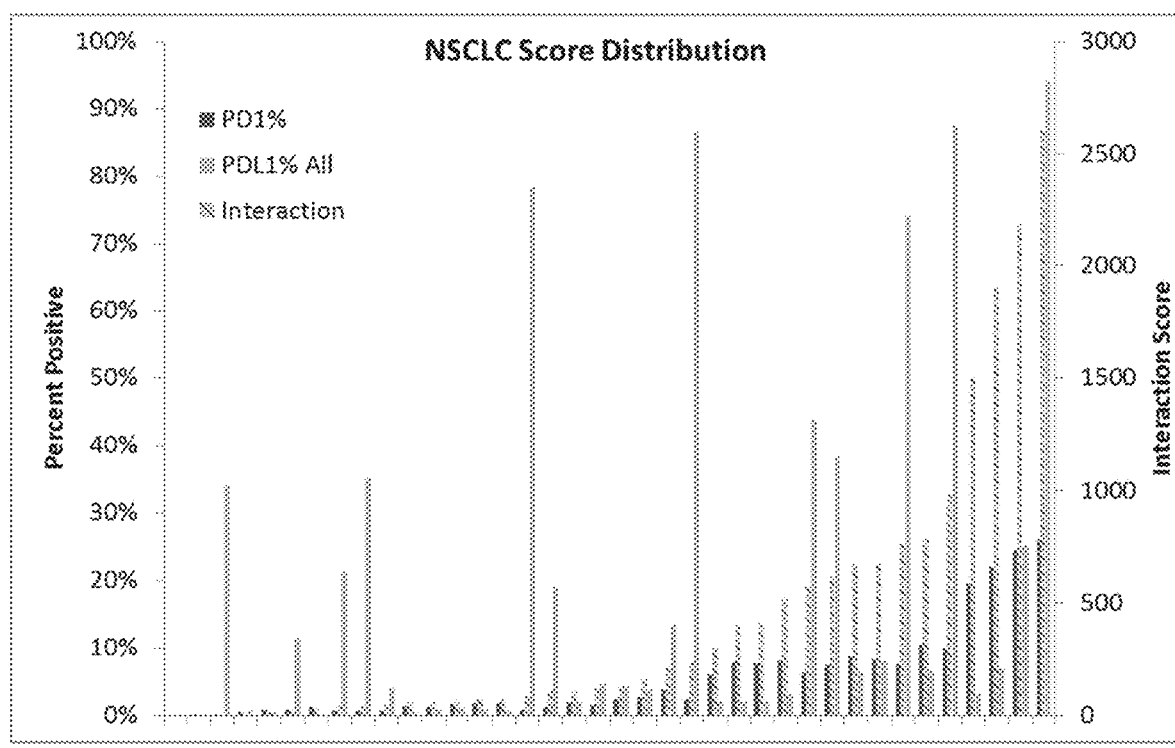
FIG. 13 shows representative PD-1/PD-L1 interaction scores from 38 non-small cell lung cancer patients.

Example 2. Sample Preparation, Imaging, and Analysis of Imaging for Non-Small Cell Lung Carcinoma Tissue Samples from Human Patients Analogous procedures as Example 1 were performed, substituting the mouse anti-S100 directly labeled with 488 dye with mouse anti-pan cytokeratin directly labeled with 488 dye for epithelial tumor samples. Interaction scores for 38 samples are shown in FIG. 13.

Example 3. Sample Preparation, Imaging, and Analysis of Imaging for Tissue Samples with Cells Expressing PD-L1 and Cells Expressing CD80

Sample preparation Formalin fixed paraffin embedded (FFPE) tissue samples were dewaxed, rehydrated and antigen retrieval was performed with elevated temperature conditions. Staining was then performed where the following steps were carried out. First, tissues were subjected to CTLA-4 expression detection using 20 pairs of hybridization probes spanning approximately 1 kb of the CTLA-4 mRNA using RNAScope® (Advanced Cell Diagnostics). In situ hybridization was visualized with TSA-Cy®3. The slides were washed and any residual HRP was then quenched using two washes of fresh 100 mM benzhydrazide with 50 mM hydrogen peroxide. The slides were again washed before staining with a mouse anti-CD80 primary antibody. Slides were washed and then incubated with an anti-mouse HRP secondary antibody. Slides were washed and then CD80 staining was detected using TSA-Cy® 5 (Perkin Elmer). Any residual HRP was then quenched using two washes of fresh 100 mM benzhydrazide with 50 mM hydrogen peroxide. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-AlexaFluor488® (Life Technologies). Slides were washed a final time before they were cover-slipped with mounting media and allowed to dry overnight at room temperature.

Figure 20:
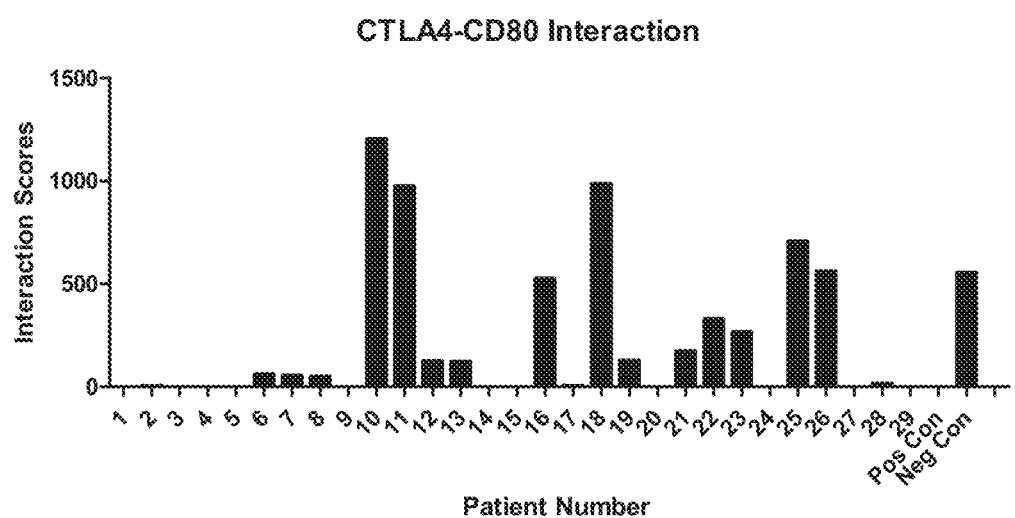
FIG. 20 shows a non-limiting example of CTLA-4/CD80 interaction scores from 29 metastatic melanoma patients.

Analogous imaging and analysis procedures as Example 1 were performed, imaging across DAPI, FITC, Cy® 3, and Cy® 5 wavelengths. Expression of CTLA-4 and CD80 was used to develop an enrichment algorithm for acquiring 20× images. Analysis was performed to determine CTLA-4/CD80 interaction scores by measuring the total area, in pixels, of CTLA-4 and CD3 positive cells within the proximity of CD80 positive cells divided by the total area, in pixels, of the CD3 positive cells, multiplied by a factor of 10,000. Results are shown in FIG. 20.

Example 4. Sample Preparation, Imaging, and Analysis of Imaging for Tissue Samples with Cells Expressing CTLA-4 and Cells Expressing CD80

Analogous procedures as Example 1 are performed, substituting the staining and analysis of PD-L1 and PD-1 with the staining and analysis of CTLA-4 and CD80.

Example 5. Sample Preparation, Imaging, and Analysis of Imaging for Tissue Samples with Cells Expressing PD-L2 and Cells Expressing PD-1

Analogous procedures as Example 1 are performed, substituting the staining and analysis of PD-L1 with the staining and analysis of PD-L2.

Example 6. Sample Preparation, Imaging, and Analysis of Imaging for Tissue Samples with Cells Expressing CTLA-4 and Cells Expressing CD86

Analogous procedures as Example 1 are performed, substituting the staining and analysis of PD-L1 and PD-1 with the staining and analysis of CTLA-4 and CD86.

Example 7. Sample Preparation, Imaging, and Analysis of Imaging for Tissue Samples with Cells Expressing LAG-3 and Cells Expressing HLA-DR Analogous procedures as Example 1 are performed, substituting the staining and analysis of PD-L1 and PD-1 with the staining and analysis of LAG-3 and HLA-DR.

Example 8. Sample Preparation, Imaging, and Analysis of Imaging for Tissue Samples with Cells Expressing TIM-3 and Cells Expressing Galectin 9

Analogous procedures as Example 1 are performed, substituting the staining and analysis of PD-L1 and PD-1 with the staining and analysis of TIM-3 and Galectin 9.

Example 9. Sample Preparation, Imaging, and Analysis of Imaging for Tissue Samples with Cells Expressing 41BB and Cells Expressing 4.1BBL Analogous procedures as Example 1 are performed, substituting the staining and analysis of PD-L1 and PD-1 with the staining and analysis of 41BB and 4.1BBL.

Example 10. Sample Preparation, Imaging, and Analysis of Imaging for Tissue Samples with Cells Expressing OX40 and Cells Expressing OX40L Analogous procedures as Example 1 are performed, substituting the staining and analysis of PD-L1 and PD-1 with the staining and analysis of OX40 and OX40L.

Example 11. Sample Preparation, Imaging, and Analysis of Imaging for Tissue Samples with Cells Expressing CD40 and Cells Expressing CD40L Analogous procedures as Example 1 are performed, substituting the staining and analysis of PD-L1 and PD-1 with the staining and analysis of CD40 and CD40L.

Example 12. Sample Preparation, Imaging, and Analysis of Imaging for Tissue Samples with Cells Expressing ICOS and Cells Expressing ICOSL Analogous procedures as Example 1 are performed, substituting the staining and analysis of PD-L1 and PD-1 with the staining and analysis of ICOS and ICOSL.

Example 13. Sample Preparation, Imaging, and Analysis of Imaging for Tissue Samples with Cells Expressing GITR and Cells Expressing GITRL Analogous procedures as Example 1 are performed, substituting the staining and analysis of PD-L1 and PD-1 with the staining and analysis of GITR and GITRL.

Example 14. Sample Preparation, Imaging, and Analysis of Imaging for Tissue Samples with Cells Expressing HLA-DR and Cells Expressing TCR Analogous procedures as Example 1 are performed, substituting the staining and analysis of PD-L1 and PD-1 with the staining and analysis of HLA-DR and TCR.

Example 15. Sample Preparation, Imaging, and Analysis of Imaging for Tissue Samples with Cells Expressing PD-1, PD-L1, and CD3

Figure 21:
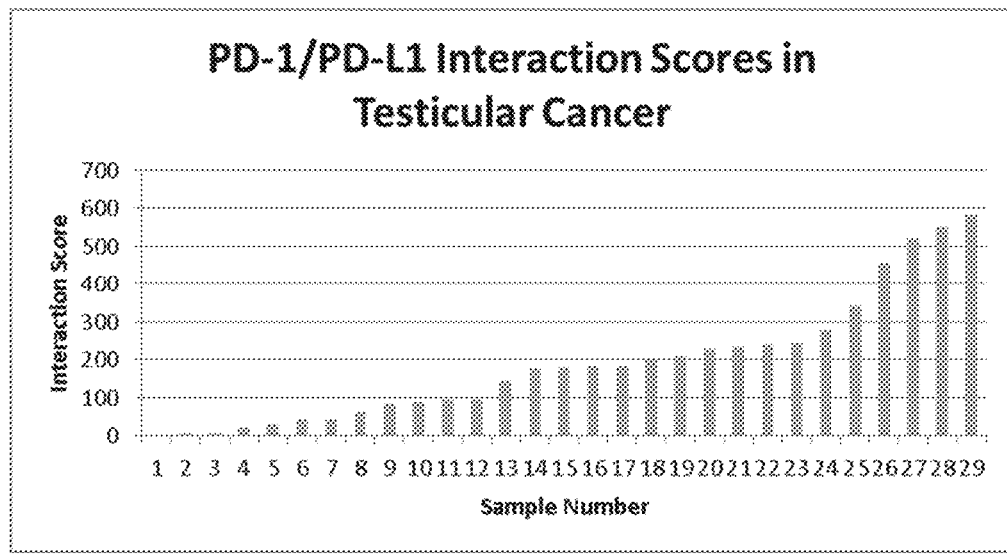
FIG. 21 shows a non-limiting example of PD-1/PD-L1 interaction scores from 29 patients with testicular carcinoma.

Analogous procedures as Example 1 were performed without the mouse anti-S100 antibody. Instead, after PD-L1 detection, primary and secondary antibodies were removed via microwave. Slides were then stained with rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected with TSA-AlexaFluor488 (Life Technologies). Imaging and analysis were analogous to Example 1 where the spatial proximity (e.g interaction score) was calculated by dividing the area of PD-L1 positive cells in the PD-L1 positive area, measured in pixels, by the area of all nucleated cells, measured in pixels, multiplied by a factor of 10,000. Interaction scores for 29 samples are shown in FIG. 21.

Para. A. A method of scoring a sample comprising tumor tissue taken from a cancer patient comprising:
  (i) using the sample comprising tumor tissue taken from the cancer patient, determining a score representative of a spatial proximity between at least one pair of cells, a first member of the at least one pair of cells expressing a first biomarker and a second member of the at least one pair of cells expressing a second biomarker that is different from the first biomarker; and
  (ii) recording the score, which score when compared to a threshold value is indicative of a likelihood that the cancer patient will respond positively to immunotherapy.

Para. B. The method of Para. A in which the first member of the at least one pair of cells comprises a tumor cell and the second member of the at least one pair of cells comprises a non-tumor cell.

Para. C. The method of Para. B in which the non-tumor cell comprises an immune cell.

Para. D. The method of Para. A in which the first and second members of the at least one pair of cells comprise immune cells.

Para. E. The method of Para. A in which the first member of the at least one pair of cells comprises a tumor cell, a myeloid cell, or a stromal cell and the second member of the at least one pair of cells comprises an immune cell.

Para. F. The method of Para. E in which the tumor cell, myeloid cell, or stromal cell expresses PD-L1 and the immune cell expresses PD-1.

Para. G. The method of any one of Paras. A-F in which the spatial proximity is assessed on a pixel scale.

Para. H. The method of any one of Paras. A-G in which the spatial proximity between the at least one pair of cells ranges from about 1 pixel to about 100 pixels.

Para. I. The method of any one of Paras. A-F in which the spatial proximity between the at least one pair of cells ranges from about 0.5 µm to about 50 µm.

Para. J. The method of Para. A in which the determining step comprises:
  (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view;
  (ii) for each of the selected fields of view, dilating fluorescence signals attributable to the first biomarker by a margin sufficient to encompass proximally located cells expressing the second biomarker; and
  (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

Para. K. The method of Para. J in which each of the fluorescence tags is directed to a specific biomarker.

Para. L. The method of Para. J or Para. K, in which the plurality of fluorescence tags comprises a first fluorescence tag for the first biomarker and a second fluorescence tag for the second biomarker.

Para. M. The method of any one of Paras. J-L in which the margin ranges from about 1 to about 100 pixels.

Para. N. The method of any one of Paras. J-M in which the proximally located cells expressing the second biomarker are within about 0.5 to about 50 µm of a plasma membrane of the cells that express the first biomarker.

Para. O. The method of any one of Paras. J-N in which the first total area is measured in pixels.

Para. P. The method of any one of Paras. J-O in which the normalization factor is a second total area for all non-tumor cells from each of the selected fields of view.

Para. Q. The method of any one of Paras. J-O in which the normalization factor is a second total area for all cells from each of the selected fields of view which have a capacity to express the second biomarker.

Para. R. The method of Para. P or Para. Q in which the second total area is measured in pixels.

Para. S. The method of any one of Paras. J-R in which the predetermined factor is $10^4$.

Para. T. The method of Para. A in which the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof.

Para. U. The method of Para. T in which the first member of the at least one pair of cells expresses PD-L1 and the second member of the at least one pair of cells expresses PD-1.

Para. V. The method of Para. T in which the first member of the at least one pair of cells expresses PD-L1 and the second member of the at least one pair of cells expresses CD80.

Para. W. The method of Para. T in which the first member of the at least one pair of cells expresses CTLA-4 and the second member of the at least one pair of cells expresses CD80.

Para. X. The method of Para. T in which the first member of the at least one pair of cells expresses PD-L2 and the second member of the at least one pair of cells expresses PD-1.

Para. Y. The method of Para. T in which the first member of the at least one pair of cells expresses CTLA-4 and the second member of the at least one pair of cells expresses CD86.

Para. Z. The method of Para. T in which the first member of the at least one pair of cells expresses LAG-3 and the second member of the at least one pair of cells expresses HLA-DR.

Para. AA. The method of Para. T in which the first member of the at least one pair of cells expresses TIM-3 and the second member of the at least one pair of cells expresses Galectin 9.

Para. AB. The method of Para. T in which the first member of the at least one pair of cells expresses 41BB and the second member of the at least one pair of cells expresses 4.1BBL.

Para. AC. The method of Para. T in which the first member of the at least one pair of cells expresses OX40 and the second member of the at least one pair of cells expresses OX40L.

Para. AD. The method of Para. T in which the first member of the at least one pair of cells expresses CD40 and the second member of the at least one pair of cells expresses CD40L.

Para. AE. The method of Para. T in which the first member of the at least one pair of cells expresses ICOS and the second member of the at least one pair of cells expresses ICOSL.

Para. AF. The method of Para. T in which the first member of the at least one pair of cells expresses GITR and the second member of the at least one pair of cells expresses GITRL.

Para. AG. The method of Para. T in which the first member of the at least one pair of cells expresses HLA-DR and the second member of the at least one pair of cells expresses TCR.

Para. AH. The method of any one of Paras. A-AG in which the threshold value ranges from about 500 to about 5000.

Para. AI. The method of Para. AH in which the threshold value is about 900 plus or minus 100.

Para. AJ. The method of any one of Paras. A-AI in which the immunotherapy comprises immune checkpoint therapy.

Para. AK. A method of determining a score representative of a spatial proximity between at least one pair of cells selected from among a plurality of cells present in a predetermined number of fields of view available from a sample comprising tumor tissue, which sample is taken from a cancer patient, the method comprising:
  (i) selecting a predetermined number of fields of view available from a sample comprising tumor tissue taken from a cancer patient, which is stained with a plurality of fluorescence tags, which selection is biased toward selecting fields of view that contain a greater number of cells that express a first specific biomarker relative to other fields of view;
  (ii) for each of the selected fields of view, dilating fluorescence signals attributable to the first specific biomarker by a margin sufficient to encompass proximally located cells expressing a second specific biomarker; and
  (iii) dividing a first total area for all cells from each of the selected fields of view, which express the second specific biomarker and are encompassed within the dilated fluorescence signals attributable to the cells expressing the first specific biomarker, with a normalization factor, and multiplying the resulting quotient by a predetermined factor to arrive at a spatial proximity score.

Para. AL. The method of Para. AK in which each of the fluorescence tags is directed to a specific biomarker.

Para. AM. The method of Para. AK or Para. AL in which the plurality of fluorescence tags comprises a first fluorescence tag for the first biomarker and a second fluorescence tag for the second biomarker.

Para. AN. The method of any one of Paras. AK-AM in which one or more fluorescence tags comprise a fluorophore conjugated to an antibody having a binding affinity for a specific biomarker or another antibody.

Para. AO. The method of any one of Paras. AK-AM in which each fluorescence tag comprises a fluorophore independently selected from one or more of the group consisting of DAPI, Cy® 2, Cy® 3, Cy® 3.5, Cy® 5, FITC, TRITC, a 488 dye, a 555 dye, a 594 dye, and Texas Red.

Para. AP. The method of any one of Paras. AK-AO in which the margin ranges from about 1 to about 100 pixels.

Para. AQ. The method of any one of Paras. AK-AP in which the proximally located cells expressing the second specific biomarker are within about 0.5 to about 50 µm of a plasma membrane of the cells that express the first specific biomarker.

Para. AR. The method of any one of Paras. AK-AQ in which the first total area is measured in pixels.

Para. AS. The method of any one of Paras. AK-AP in which the normalization factor is a second total area for all non-tumor cells from each of the selected fields of view.

Para. AT. The method of any one of Paras. AK-AP in which the normalization factor is a second total area for all cells from each of the selected fields of view which have a capacity to express the second specific biomarker.

Para. AU. The method of Para. AS or Para. AT in which the second total area is measured in pixels.

Para. AV. The method of any one of Paras. AK-AU in which the predetermined factor is $10^4$.

Para. AW. The method of Para. AK in which the spatial proximity score (SPS) is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker.

Para. AX. The method of Para. AK in which the first specific biomarker comprises a tumor and non-tumor marker and the second specific biomarker comprises a non-tumor marker.

Para. AY. The method of Para. A, wherein the method provides a superior predictive power compared to a quantitation of expression of the first biomarker or a quantitation of expression of the second biomarker.

Para. AZ. The method of Para. AK, wherein the method provides a superior predictive power compared to a quantitation of expression of the first specific biomarker or a quantitation of expression of the second specific biomarker.

Para. BA. The method of Para. AY or Para. AZ, wherein the predictive power is quantified as a positive predictive value, a negative predictive value, or a combination thereof.

Para. BB. The method of Para. BA, wherein the positive predictive value is 65% or greater.

Para. BC. The method of Para. BB, wherein the positive predictive value is 70% or greater.

Para. BD. The method of Para. BC, wherein the positive predictive value is 75% or greater.

Para. BE. The method of Para. BA, wherein the negative predictive value is 65% or greater.

Para. BF. The method of Para. BE, wherein the negative predictive value is 80% or greater.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of determining a score representative of a spatial proximity between at least one pair of cells selected from among a plurality of cells present in a predetermined number of fields of view available from a sample comprising tumor tissue, which sample is taken from a cancer patient, the method comprising:
    (i) selecting a predetermined number of fields of view available from a sample comprising tumor tissue taken from a cancer patient, which is stained with a plurality of fluorescence tags, which selection is biased toward selecting fields of view that contain a greater number of cells that express a first specific biomarker relative to other fields of view;
    (ii) for each of the selected fields of view, dilating fluorescence signals attributable to the first specific biomarker from all cells that are positive for the first specific biomarker by a margin sufficient to encompass proximally located cells expressing a second specific biomarker; and
    (iii) dividing a first total area for all cells from each of the selected fields of view, which express the second specific biomarker and are encompassed within the dilated fluorescence signals attributable to the cells expressing the first specific biomarker, with a normalization factor, and multiplying the resulting quotient by a predetermined factor to arrive at a spatial proximity score.

2. The method of claim 1, in which the plurality of fluorescence tags comprises a first fluorescence tag for the first specific biomarker and a second fluorescence tag for the second specific biomarker.

3. The method of claim 1, in which one or more of the fluorescence tags comprise a fluorophore conjugated to an antibody having a binding affinity for a specific biomarker or another antibody.

4. The method of claim 1, in which each fluorescence tag comprises a fluorophore independently selected from one or more of the group consisting of DAPI, CY® 2, CY® 3, CY® 3.5, CY® 5, FITC, TRITC, a 488 dye, a 555 dye, a 594 dye, and Texas Red.

5. The method of claim 1, in which the margin ranges from about 1 to about 100 pixels.

6. The method of claim 1, in which the proximally located cells expressing the second specific biomarker are within about 0.5 to about 50 µm of a plasma membrane of the cells that express the first specific biomarker.

7. The method of claim 1, in which the first total area is measured in pixels.

8. The method of claim 1, in which the normalization factor is a second total area for all non-tumor cells from each of the selected fields of view.

9. The method of claim 1, in which the normalization factor is a second total area for all cells from each of the selected fields of view which have a capacity to express the second specific biomarker.

10. The method of claim 8, in which the second total area is measured in pixels.

11. The method of claim 1, in which the predetermined factor is $10^4$.

12. The method of claim 1, in which the spatial proximity score (SPS) is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker.

13. The method of claim 1, in which the first specific biomarker comprises a tumor and non-tumor marker and the second specific biomarker comprises a non-tumor marker.

14. The method of claim 1, in which the first specific biomarker is selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second specific biomarker is selected from the group consisting of PD-1, TIM3, LAG3, 41BB, OX40, CTLA-4, CD40L, CD28, GITR, ICOS, CD28, and combinations thereof.

15. The method of claim 1, wherein the method provides a superior predictive power compared to a quantitation of expression of the first biomarker or a quantitation of expression of the second biomarker.

16. The method of claim 15, wherein the predictive power is quantified as a positive predictive value, a negative predictive value, or a combination thereof.

17. The method of claim 16, wherein the positive predictive value or the negative predictive power is 65% or greater.

18. The method of claim 16, wherein the positive predictive value or the negative predictive power is 70% or greater.

19. The method of claim 16, wherein the positive predictive value or the negative predictive power is 75% or greater.

20. The method of claim 1, wherein step (ii) comprises
   a) generating a mask of all cells that are positive for the first specific biomarker; and
   b) dilating the mask of all cells that are positive for the first specific biomarker to generate a dilated mask representative of a predetermined proximity within which an interacting cell positive for the second specific biomarker may be found.

* * * * *